United States Patent [19]
Moshe et al.

[11] Patent Number: 6,107,809
[45] Date of Patent: *Aug. 22, 2000

[54] DEVICE AND METHOD FOR DETERMINING THE MOISTURE CONTENT OF TOBACCO

[75] Inventors: Danny S. Moshe, Kiryat Ono; Alexander Greenwald, Nazareth-Illit, both of Israel

[73] Assignee: Malcam Ltd., Tel Aviv, Israel

[ * ] Notice: This patent is subject to a terminal disclaimer.

[21] Appl. No.: 09/126,384

[22] Filed: Jul. 30, 1998

Related U.S. Application Data

[63] Continuation-in-part of application No. 08/974,983, Nov. 20, 1997, Pat. No. 6,025,724, and a continuation-in-part of application No. 08/777,872, Dec. 31, 1996, Pat. No. 5,845,529, which is a continuation-in-part of application No. 08/503,838, Jul. 18, 1995, Pat. No. 5,621,330.

[51] Int. Cl.$^7$ ..................................................... G01N 5/02
[52] U.S. Cl. .......................... 324/640; 324/637; 324/639; 73/73; 73/76
[58] Field of Search ..................... 324/640, 637, 324/639; 73/73, 76

[56] References Cited

U.S. PATENT DOCUMENTS 3,766,471  10/1973  Pullman ................................. 324/694
5,621,330   4/1997  Greenwald et al. .................... 324/640
5,845,529  12/1998  Moshe et al. .......................... 324/640

*Primary Examiner*—Josie Ballato
*Assistant Examiner*—James Kerveros
*Attorney, Agent, or Firm*—Mark M. Friedman

[57] ABSTRACT

A method of determining the moisture content of a module of tobacco material, the method comprising the steps of: (a) transmitting a plurality of microwaves substantially through a portion of the module, such that the microwaves are transmitted microwaves; (b) receiving the transmitted microwaves such that the microwaves are received microwaves; (c) determining a phase shift and an attenuation from the received microwaves; (d) repeating steps (a) to (c) for at least a portion of the material on the module, such that a plurality of phase shifts and a plurality of attenuations is obtained; (e) using at least one empirical factor selected from the group consisting of weight of the module, temperature of the module, shape of the module and type of the material to correct the plurality of attenuations, producing a plurality of corrected attenuations; (f) calculating a raw moisture content of the material from the corrected attenuations; (g) determining a density of the material from the phase shifts; and (h) calculating a final moisture content of the material from the density and from the raw moisture content.

18 Claims, 16 Drawing Sheets

FIG. 3
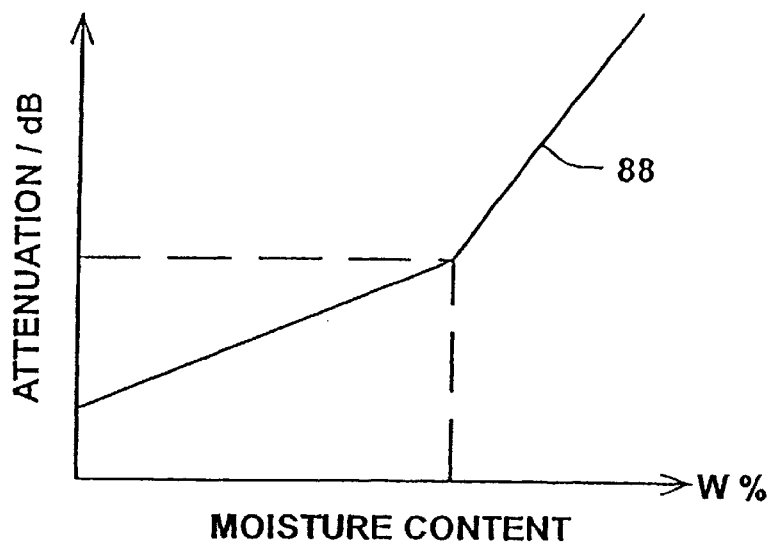
FIG. 4A
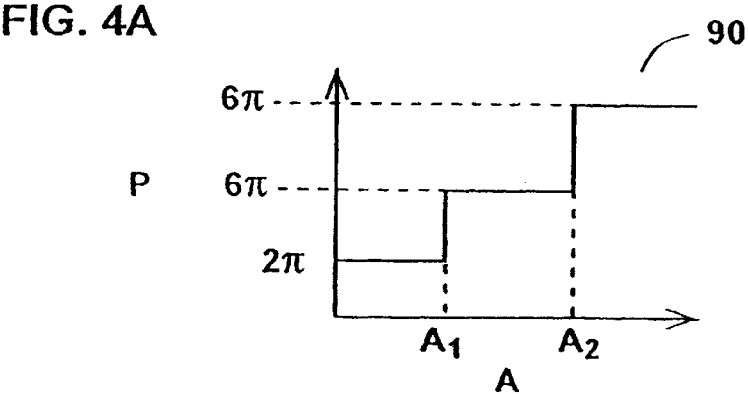
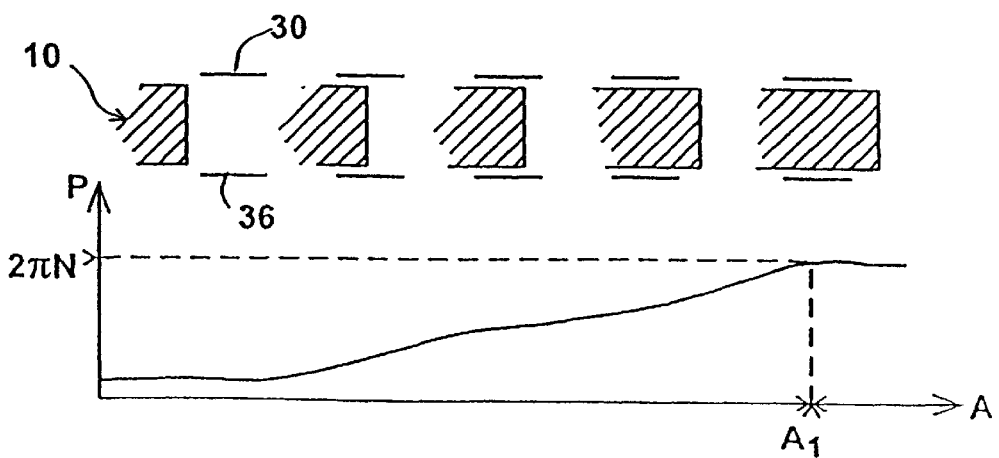
FIG. 4B

DEVICE AND METHOD FOR DETERMINING THE MOISTURE CONTENT OF TOBACCO

This is a Continuation-in-Part of U.S. patent application Ser. No. 08/974,983, filed on Nov. 20, 1997, now U.S. Pat. No. 6,025,724 and of U.S. patent application Ser. No. 08/777,872, filed on Dec. 31, 1996, now U.S. Pat. No. 5,845,529 which is a Continuation-in-Part of U.S. patent application Ser. No. 08/503,838, filed on Jul. 18, 1995, now U.S. Pat. No. 5,621,330.

FIELD AND BACKGROUND OF THE INVENTION

The present invention relates to a device and method for determining the moisture content of tobacco, particularly tobacco in the form of bales.

Many different types of synthetic and organic materials are the basis for the construction of many different manufactured products. These materials must be gathered, transported and stored before being used in the manufacturing process. The manufacturing process itself may require multiple procedures, first to prepare the raw material, and then to use the processed material in the formation of the actual product. Many of these procedures are dependent upon the moisture content of the material. If the moisture content is too high, for example, the material may decompose during storage and transportation, before it can be used. If the moisture content is too low, processing and use of the material may be difficult.

Synthetic and organic materials whose behavior depends upon their moisture content include cotton, paper, wool, seeds, tobacco, pharmaceuticals and synthetic fibers. As an example, tobacco can be considered, although it will be appreciated that similar examples could be given for any of the above materials.

Tobacco is typically stored in large bales before being processed to manufacture cigarettes, pouch tobacco, chewing tobacco and other tobacco products. As it is stored, the chemical composition of the tobacco material can alter as a result of various reactions involving compounds found in tobacco. Some of these reactions can produce chemical products which are particularly harmful to people who smoke, while other products are detrimental to the taste and shelf life of the tobacco. Indeed, the relevant regulatory authority in each country, such as the FDA (Food and Drug Administration) for the United States of America, frequently request maximum levels of the harmful chemical compounds. If the concentration of one or more of these components exceeds this limit, the regulatory authority may not permit the tobacco to be sold within the country. The rate and extent of these reactions may be altered by the moisture content of the tobacco. Therefore, the tobacco industry must process the tobacco within a relatively narrow range of moisture values, in order to comply with these regulations and in order to maintain the quality of the tobacco. Thus, clearly the concentration of these components within the tobacco must be monitored, and if possible the tobacco must be processed substantially before such components increase to potentially harmful levels.

The rate and extent of such reactions is often influenced by the moisture content of the tobacco. Therefore, in order to optimally store and process the tobacco, measurements of the moisture content of the tobacco may be performed. Unfortunately, currently available methods for the measurement of the moisture content of the tobacco involve the removal of samples from the tobacco bale, and the determination of the moisture content of the samples alone. Such sampling can be very inaccurate, since the moisture content of the tobacco may vary widely throughout the bale, thereby yielding misleading results. In addition, measurement of the moisture content of the loose tobacco leaves is also important, yet is also difficult to determine by sampling small portions of material. Preferably, such bulk volumes of material would be measured as the leaves pass through a silo, for example on a conveyor belt, rather than by sampling the material. Thus, currently available methods for measuring the moisture content of both tobacco bales and bulk volumes of loose leaves have significant drawbacks.

A far more useful method for determining the moisture content of tobacco would involve the measurement of the moisture content throughout the bale, such that a more accurate moisture measurement could be made. Such a method would also preferably preserve the tobacco material, such that the tobacco would not be destroyed during the process of measuring the moisture content. Furthermore, the regulation of the moisture content can in turn control the level of the various chemical compounds which are produced as a result of the previously described chemical processes. Thus, an accurate determination of the moisture content of the tobacco is necessary for proper storage and manufacture of tobacco products.

There is thus widely recognized need for, and it would be highly advantageous to have, a method for measuring the moisture content of tobacco, which would enable the moisture content to be determined throughout the structure, such as the bale, substantially without destroying the tobacco material.

SUMMARY OF THE INVENTION

According to the present invention there is provided a method of determining a moisture content of tobacco material, the method comprising the steps of: (a) transmitting a plurality of microwaves substantially through at least a portion of the material, such that the microwaves are transmitted microwaves; (b) receiving the transmitted microwaves such that the microwaves are received microwaves; (c) determining an attenuation from the received microwaves; (d) using at least one empirical factor selected from the group consisting of weight of the material, temperature of the material, structure of the material and type of the tobacco material to correct the attenuation, producing a corrected attenuation; and (e) calculating the moisture content of the tobacco material from the corrected attenuation. Preferably, the step of determining the attenuation further comprises the step of determining a phase shift from the received microwaves.

According to preferred embodiments of the present invention, the step of determining the attenuation further comprises the step of: (i) repeating steps (a) to (c) for at least a portion of the material on the bale, such that a plurality of phase shifts and a plurality of attenuations are obtained, and such that a plurality of corrected phase shifts are produced according to the plurality of phase shifts Preferably, the method further comprises the step of: (ii) determining a density of the material from the phase shifts; and (iii) calculating a final moisture content of the material from the density and from the raw moisture content.

Alternatively and preferably, the material features an internal structure and an irregularity of the density of the internal structure is calculated by comparing one of the plurality of phase shifts to a previous value of the phase shifts, such that the irregularity is detected if one of the plurality of phase shifts differs from the previous value. More preferably, the irregularity of the density of the internal structure indicates that the material has been processed unevenly, which can result in problems during the process of fermentation due to uneven moisture content of the material, thereby affecting the overall quality of the tobacco.

According to other preferred embodiments of the present invention, a first phase shift is determined for microwave radiation of a first frequency $F_1$, and a second phase shift is determined for microwave radiation of a second frequency $F_2$, the first phase shift being corrected to form a first measured phase shift according to the equation:

$$Ph_{F_1} = \frac{\Delta Ph(F_2) - \Delta Ph(F_1)}{F_2 - F_1} F_1$$

wherein $Ph_{F1}$ is the measured phase shift for the first frequency $F_1$, and $\Delta Ph(F_1)$ and $\Delta Ph(F_2)$ are the phase shifts for $F_1$ and $F_2$; and wherein a first corrected phase shift is formed according to the following equation:

$$(Ph_{F1} \bmod(360)*360) + \Delta Ph(F_1) = P_{true}$$

such that $P_{true}$ is the first corrected phase shift. Preferably, the moisture content is determined according to a ratio of the attenuation and the corrected phase shift.

More preferably, an empirical curve of a relation between the ratio and the moisture content is provided, such that the moisture content is determined according to the ratio by using the empirical curve.

Preferably, the tobacco material is contained in a module.

More preferably, the at least one empirical factor is a plurality of empirical factors selected from the group consisting of weight of the module, type of the material, structure of the module, location of the module relative to the plurality of microwaves and temperature, and the factors are stored in a database.

Most preferably, the corrected attenuations and the phase shifts are further corrected by removing attenuations and phase shifts produced after the plurality of microwaves passes through an edge of the module, such that a first portion of the plurality of microwaves passes through the portion of the module and a second portion of the plurality of microwaves substantially does not pass through the portion of the module.

Preferably, the step of determining the density includes detecting a defect in the material, the defect being selected from the group consisting of irregular moisture distribution within an interior of the material and presence of a foreign body inside the material.

According to another embodiment of the present invention, there is provided a method for determining a moisture content of tobacco material, the method comprising the steps of: (a) transmitting a plurality of microwaves substantially through at least a portion of the material, such that the microwaves are transmitted microwaves; (b) receiving the transmitted microwaves such that the microwaves are received microwaves; (c) determining an attenuation from the received microwaves; (d) determining a phase shift from the received microwaves; and (e) calculating the moisture content of the tobacco material from a ratio of the attenuation and the phase shift.

Preferably, the step of calculating the moisture content further comprises the steps of: (i) providing an empirical curve of a relation between the ratio and the moisture content; (ii) determining the moisture content according to the ratio by using the empirical curve.

More preferably, the step of determining the attenuation further comprises the step of: (i) using at least one empirical factor selected from the group consisting of weight of the material, temperature of the material, structure of the material and type of the tobacco material to correct the attenuation, producing a corrected attenuation.

Most preferably, the step of determining the phase shift further comprises the steps of: (i) determining a first phase shift for microwave radiation of a first frequency $F_1$; (ii) determining a second phase shift for microwave radiation of a second frequency $F_2$; and (iii) correcting the first phase shift to form a first corrected phase shift according to the equation:

$$Ph_{F_1} = \frac{\Delta Ph(F_2) - \Delta Ph(F_1)}{F_2 - F_1} F_1$$

wherein $Ph_{F1}$ is the corrected phase shift for the frequency $F_1$;
and $\Delta Ph(F_1)$ and $\Delta Ph(F_2)$ are the phase shifts for $F_1$ and $F_2$.

According to yet another embodiment of the present invention, there is provided a method for determining a moisture content of tobacco material, the method comprising the steps of: (a) transmitting a plurality of microwaves of a plurality of frequencies substantially through a portion of the material, the microwaves of each of the plurality of frequencies being transmitted sequentially such that the microwaves are transmitted microwaves of a particular frequency; (b) receiving the transmitted microwaves of the particular frequency such that the microwaves are received microwaves of the particular frequency and such that the transmitted microwaves from the plurality of frequencies are received; (c) determining an attenuation from the received microwaves of each of the particular frequencies, such that a plurality of attenuations is determined; (d) determining a phase shift from the received microwaves of each of the particular frequencies, such that a plurality of phase shifts is determined; (e) correcting each of the plurality of phase shifts according to the plurality of phase shifts, such that first phase shift is determined for microwave radiation of a first frequency $F_1$, and a second phase shift is determined for microwave radiation of a second frequency $F_2$, the first phase shift being corrected to form a first corrected phase shift according to the equation:

$$Ph_{F_1} = \frac{\Delta Ph(F_2) - \Delta Ph(F_1)}{F_2 - F_1} F_1$$

wherein $Ph_{F1}$ is the corrected phase shift for the first frequency $F_1$; and $\Delta Ph(F_1)$ and $\Delta Ph(F_2)$ are the phase shifts for $F_1$ and $F_2$; and (f) determining the moisture content according to a ratio of the corrected phase shift and the attenuation.

Hereinafter, the term "bale" refers to any structure in which the tobacco material is present in pressed layers and tied with ties wrapped around the structure, and includes, but is not limited to, farmer bales, in which the leaves are bound with ties alone; a case, in which the leaves are placed in crates with wooden or cardboard sides; a hogshead, in which the case has a substantially cylindrical shape; and an oriental bale. Hereinafter, the term "module" refers to any structure of material, including bales and cases.

BRIEF DESCRIPTION OF THE DRAWINGS

The invention is herein described, by way of example only, with reference to the accompanying drawings, wherein:

FIG. 3 shows an example of a calibration curve used for calculating the moisture content of the module according to the present invention;

FIGS. 4A and 4B show a phase region curve of a preferred embodiment of the present invention;

FIG. 12 shows a second exemplary embodiment of a device which can be used with the method of the present invention.

DESCRIPTION OF THE PREFERRED EMBODIMENTS

The present invention is of a method and a device which can be used to measure the moisture content and the internal structure of material on a tobacco bale, or of a bulk volume of material such as loose tobacco leaves, by using microwave radiation. Typically, a microwave radiation source is located on one side of the tobacco, such as the tobacco bale, and an antenna is located on the opposite side of the bale. The radiation source beam is transmitted through a portion of the bale and is received by the receiving antenna, which then produces a signal. This signal is used to determine the moisture content of that portion of the bale and the mass uniformity of the bale. A method for performing such moisture measurements is disclosed in U.S. Pat. No. 5,621,330, referenced herein as if incorporated in full. Additional aspects of such a method are also disclosed in U.S. Pat. Nos. 5,845,529 and 6,025,724 also referenced herein as if incorporated in full. In addition, the methods and devices described herein can also be used to measure the moisture content of a bulk volume of loose tobacco leaves, for example as these leaves travel through a silo.

The principles and operation of a method according to the present invention may be better understood with reference to the drawings and the accompanying description.

Figure 1A:
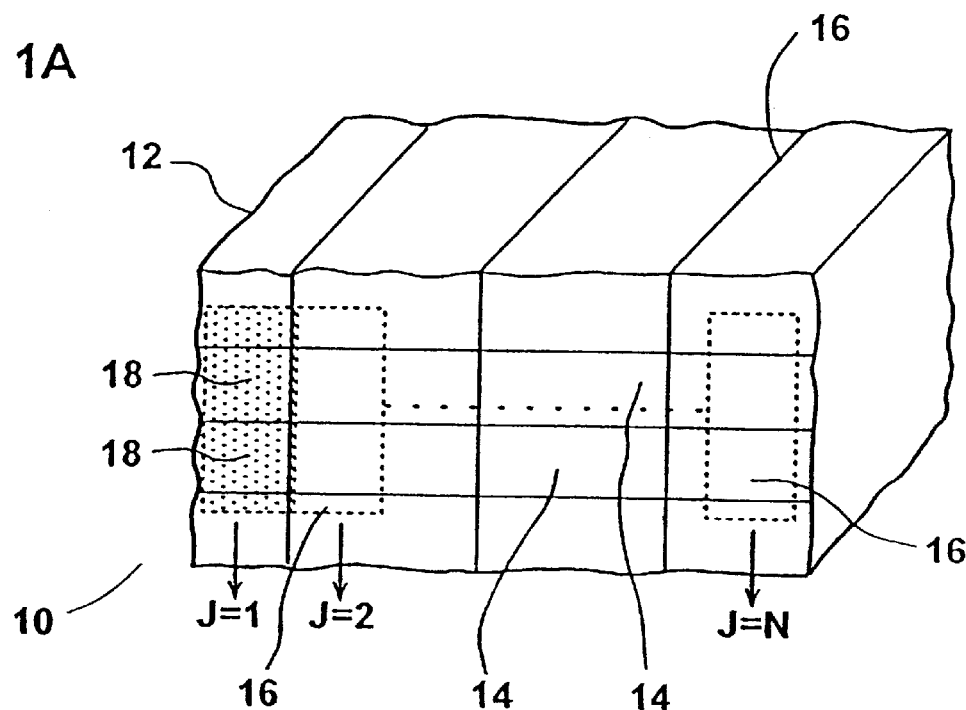
FIGS. 1A and 1B are illustrative examples of modules whose moisture can be measured by the present invention.
Figure 1B:
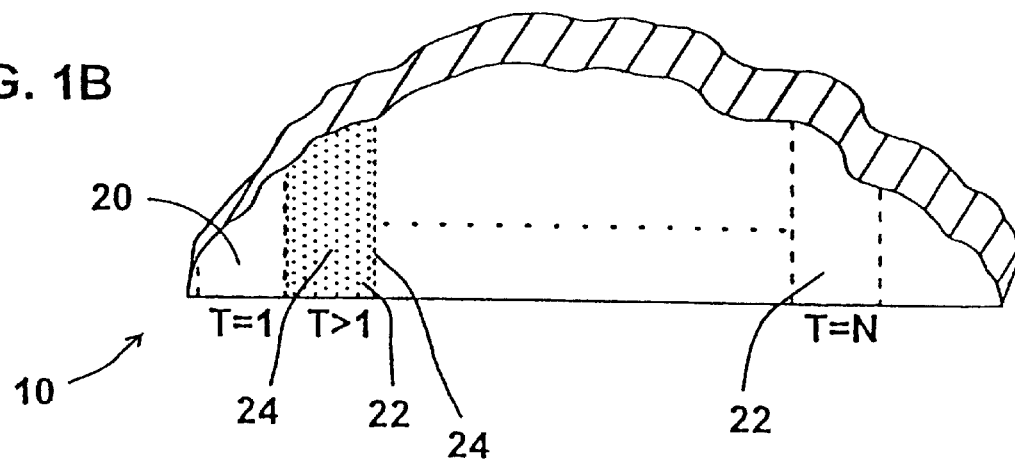

Referring now to the drawings, FIGS. 1A and 1B are illustrative examples of modules whose moisture can be measured by the present invention. FIG. 1A shows a module 10 which is a bale 12, which could for example be a bale of tobacco. Bale 12 consists of pressed layers of material 14, optionally held together with at least one tie bar 16. Tie bar 16 can be made of plastic or metal. Layers 14 can be any synthetic or organic material, including, but not limited to, tobacco, cotton, paper, processed wood, tea and synthetic fibers. For the purposes of measuring the moisture content of bale 12, bale 12 can be divided into at least one, and preferably a plurality, of areas 17. Each area 17 includes at least one measurement point 18, and preferably a plurality of measurement points 18. At each measurement point 18, the moisture content of that portion of bale 12 is determined (see FIG. 2 below).

FIG. 1B illustrates a module 10 which is a case 20. Case 20 does not have defined layers, unlike bale 12. However, case 20 can also be divided into at least one, and preferably a plurality, of areas 22. Furthermore, each area 22 can also be subdivided into at least one, and preferably a plurality, of measurement points 24. At each measurement point 24, the moisture content of that portion of case 20 is determined (see FIG. 2 below). Tobacco could also be stored in case 20.

For the purposes of discussion only, the description of the method of the present invention is limited to the measurement of the moisture content of tobacco leaves in modules such as bales, it being understood that this is not meant to be limiting in any way. These moisture measurements can be performed on the tobacco leaves in substantially any structure, including bulk volumes of loose leaves. The type of structure of the tobacco material depends partly upon the stage of the processing of the tobacco. Briefly, tobacco leaves are loose, bulk volumes of material after being harvested and threshed. The leaves are then bound into bales, after which the primary processing is performed. The primary processing stage includes cutting the tobacco. The cut tobacco is typically stored in some type of case, such as a wooden box. The secondary processing stage is then performed, in which the tobacco products such as cigarettes are manufactured. Thus, the method of the present invention can be used for the measurement of the moisture content of tobacco in substantially any stage of the processing, although specific reference is made herein to modules and bales for the purposes of discussion only.

Figure 2:
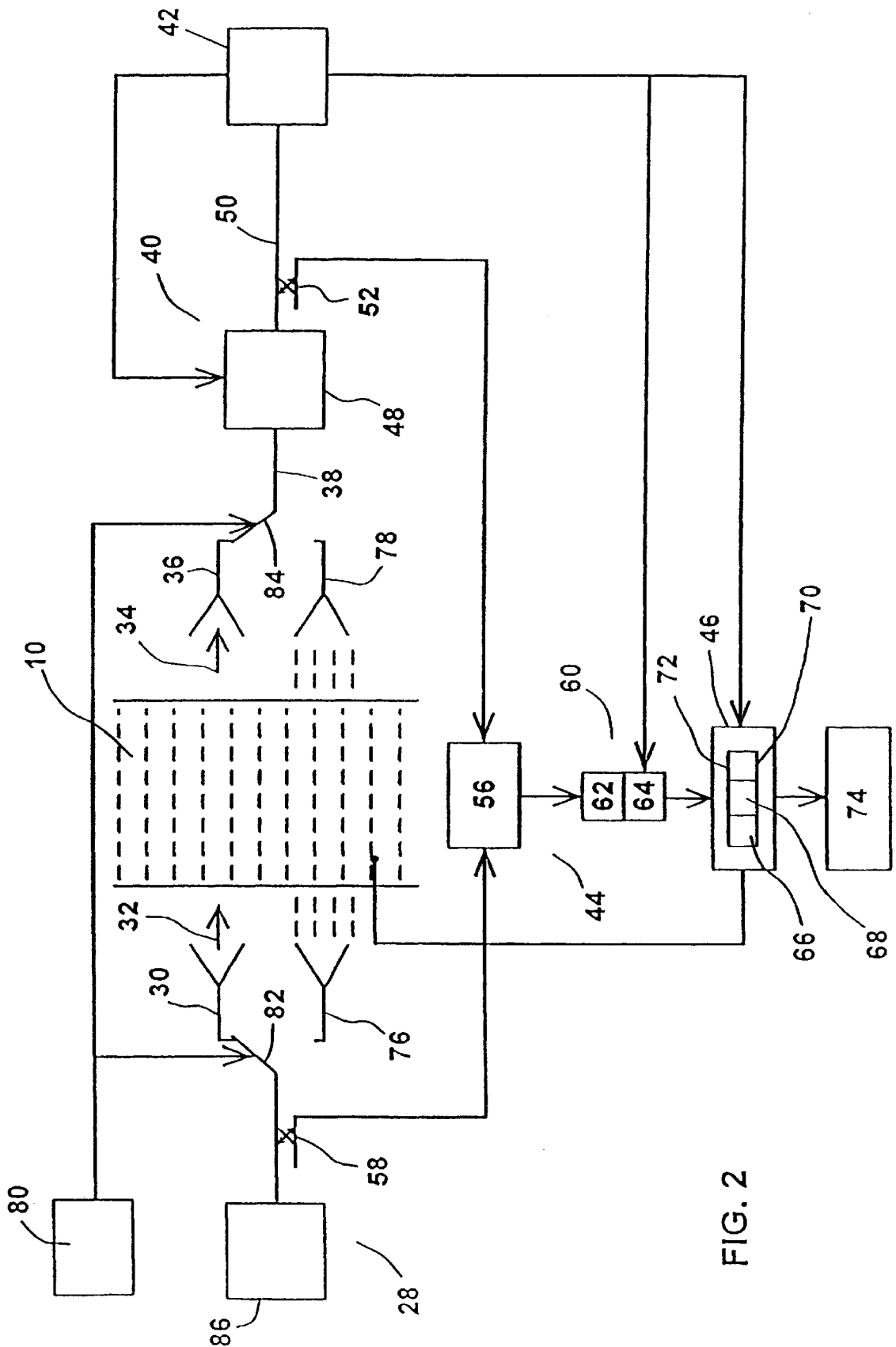
FIG. 2 is a block diagram illustrating one embodiment of the present invention.

FIG. 2 shows a device according to one embodiment of the present invention. Device 26 includes a microwave radiation source 28, shown on one side of module 10. Microwave radiation source 28 preferably includes at least one source antenna 30 for transmitting a source beam 32. Source beam 32 is directed through module 10, and passes out of module 10 as an exit beam 34. Exit beam 34 is received by at least one receiving antenna 36. Receiving antenna 36 is located on a substantially opposing side of module 10 relative to source antenna 30.

After receiving antenna 36 has received exit beam 34, receiving antenna 36 produces an antenna signal 38. Antenna signal 38 then goes to an attenuation unit 40. Attenuation unit 40 includes an attenuation measurer 42, which measures the attenuation of antenna signal 38. As source beam 32 passes through module 10, source beam 32 is attenuated. The extent of this attenuation is determined by the source beam 32, and by the moisture content of the material of module 10 elementary mass, which is the mass of the material of module 10 encountered by encountered by source beam 32. Thus, attenuation measurer 42 is actually measuring the extent to which source beam 32 is attenuated by passing through module 10.

At least a part of antenna signal 38 also goes to a phase shift determiner 44, which determines the phase shift of antenna signal 38. This phase shift is actually the phase shift caused by source beam 32 passing through module 10, so that the phase shift is the difference between the phase of source beam 32 and the phase of exit beam 34. The attenuation and the phase shift are determined according to the following equations:

$$A = 8.68\, \alpha l$$

$l$ being length of module 10, $\alpha$ being the attenuation factor for module 10.

$$P = (\beta - \beta_0) l$$

$\beta$ and $\beta_0$ being phase factors for module 10 and air, respectively.

The attenuation and the phase shift of antenna signal 38 are then used by a moisture determiner 46 to determine the moisture content of module 10.

Moisture determiner 46 uses the following equations to determine the moisture content of module 10. In these equations, A is attenuation, P is phase shift, W is moisture content, and M is the elementary mass of module 10. Equations 1 and 2 are integrated to produce equations 3 and 4. The moisture content, W, is then calculated.

$$dA = \frac{\partial A}{\partial W} dW + \frac{\partial A}{\partial m} dm$$

$$dP = \frac{\partial P}{\partial W} dW + \frac{\partial P}{\partial m} dm$$

$$A = \frac{\partial A}{\partial W} W + \frac{\partial A}{\partial m} m$$

$$P = \frac{\partial P}{\partial W} W + \frac{\partial P}{\partial m} m$$

A number of optional features can be added to device 26 in order to increase the accuracy of moisture measurements. Preferably, attenuation unit 40 includes an attenuator 48. The function of attenuator 48 is to attenuate antenna signal 38, so that antenna signal 38 becomes an attenuated antenna signal 50. A coupler 52 then splits attenuated antenna signal 38 into two portions. A first portion of attenuated antenna signal 50 goes to phase shift determiner 44. A second portion of attenuated antenna signal 50 preferably goes to attenuation measurer 42. Attenuation measurer 42 preferably determines the difference between the amplitude of attenuated antenna signal 50 and the amplitude of a constant reference signal 54. The difference between these two amplitudes determines the extent to which attenuator 48 attenuates antenna signal 38, so that the attenuation of antenna signal 38 is kept substantially constant. Such constancy is required for the proper operation of phase shift determiner 44 (see below).

As noted above, phase shift determiner 44 determines the difference, or phase shift, between the phase of source beam 32 and the phase of exit beam 34. Phase shift determiner 44 preferably includes a mixer 56, which outputs a signal which is proportional to the phase shift between source beam 32 and exit beam 34, as represented by antenna signal 38. In order for mixer 56 to receive a portion of source beam 32, microwave radiation source 28 preferably includes a second coupler 58, for splitting source beam 32 into two portions. A first portion of source beam 32 is directed through module 10 as described above. A second portion of source beam 32 is directed to mixer 56.

Phase shift determiner 44 preferably also includes a signal phase shift measurer 60. Signal phase shift measurer 60 measures the phase shift between source beam 32 and exit beam 34 from the signal output by mixer 56. In order to obtain the most accurate moisture content measurements, phase shift measurer 60 can optionally include a number of features designed to compensate for inaccuracies in the measurement of the phase shift. These features include a raw phase shift measurer 62, which determines the new phase shift. Next, a phase region determiner 64 determines the phase region of the raw phase shift from the attenuation of antenna signal 38 and produces a corrected phase shift. As measured directly from source beam 32 and exit beam 34, as represented by antenna signal 38, the phase shift can only vary from 0 to $2\pi$. However, the correct phase actually lies between $2\pi(n-1)$ and $2\pi n$, which can be from 0 to $2\pi$, but which could also be from $4\pi$ to $6\pi$, for example. Thus, the phase region, or the value of n, must be determined. Such a determination is made using an empirical phase region curve, as shown in FIG. 4 below, which relates the attenuation of antenna signal 38 to the phase region. The correct phase shift is then given to moisture determiner 46.

In order for the phase shift measurement to be accurate, the attenuation of antenna signal 38 must be kept substantially constant. Otherwise, the comparison between source beam 32 and antenna signal 38 will be artifactually altered by the attenuation of antenna signal 38.

As noted above, once the phase shift and the attenuation have been measured, moisture determiner 46 determines the moisture content of module 10. Moisture determiner 46 preferably includes a temperature sensor 66 for measuring the temperature of module 10. The type of module 10 is preferably input into moisture determiner 46 by a module type input 68. The type of module 10 is determined by the material of module 10, which is preferably tobacco, and by the form of module 10: for example, bale 12 or case 20. Finally, moisture determiner 46 preferably includes a normalizer 70. Normalizer 70 preferably includes an empiric function 72. Empiric function 72 determines the moisture content of module 10 from the temperature and type of module 10, and from the attenuation and phase shift calculated above.

The above description has treated the measurement of the moisture content of module 10 as though a single moisture measurement was made. However, preferably a plurality of such measurements are made and averaged by an averager 74. As described in FIG. 1, bale 12 can be divided into preferably a plurality of areas 17. Each area 17 is preferably subdivided into a plurality of measurement points 18. At each measurement point 18, the moisture content of that portion of bale 12 is determined according to the above description, so that a plurality of measurements are made and averaged by averager 74. A similar argument can be made for case 20, areas 22 and measurement points 24. These averaged measurements are then preferably compared to a calibration curve, of the type shown in FIG. 3, in order to obtain the moisture content of module 10. Optionally, in order to facilitate such multiple measurements, device 26 can include a conveyor, such as a conveyor belt (not shown) or a truck (not shown, see FIG. 6) to convey bale 12 between microwave radiation source 28 and receiving antenna 36.

Optionally, microwave radiation source 28 can also include a second source antenna 76. Also optionally, device 26 can also include a second receiving antenna 78. Optionally, an oscillator 80 controls a first switch 82 and a second switch 84. These optional features are used to measure the moisture content of module 10 in two parts when module 10 is too tall for a single measurement. First, oscillator 80 flips first switch 82 so that first source antenna 30 directs source beam 32, and second switch 84 so that first receiving antenna 36 produces antenna signal 38. This particular configuration is shown in FIG. 2, and is used to measure the moisture content of the lower portion of module 10. Next, oscillator 80 flips first switch 82 so that second source antenna 78 directs source beam 32. Oscillator 80 also flips second switch 84 so that second receiving antenna 78 produces antenna signal 38. Now, the moisture content of the upper portion of module 1 is measured.

Microwave radiation source 28 can also optionally include a number of features which are designed to maximize the sensitivity of the moisture content measurements, by manipulating the direction of the electric field density of source beam 32 (see also FIGS. 5A–5F). Microwave radiation source 28 can include an electric field director 86. Electric field director 86 determines a direction of the electric field density of source beam 32 relative to module 10, such that the direction of the electric field density partially determines the magnitude of the attenuation and the magnitude of the phase shift. If module 10 has layers 14 (not shown), substantially the maximum attenuation and substantially the maximum phase shift of antenna signal 38 is obtained when the electric field density is substantially perpendicular to layers 14 (not shown) of module 10. When the electric field density is substantially parallel to layers 14 (not shown) of module 10, substantially the minimum attenuation and the minimum phase shift of antenna signal 38 is obtained. Even is module 10 does not have layers 14, changing the direction of the electric field density will still alter the attenuation and phase shift of antenna signal 38, according to the orientation of the material being measured relative to the electric field density. Electric field director 86 determines the direction of the electric field density according to feedback from attenuation measurer 42. Thus, if the attenuation of antenna signal 38 is low, electric field director 86 can change the direction of the electric field density in order to compensate. Clearly, this obvious advantages in maximizing the sensitivity and accuracy of the moisture measurements.

FIG. 3 shows an illustrative example of a calibration curve 88, showing the relationship between attenuation, in dB, on the Y-axis, and moisture content, as a percentage, on the X-axis. Each calibration curve 88 is empirically determined for each type of module 10 (for example bale or case), and for each type of material (for example, tobacco). The moisture content of module 10 is then determined from calibration curve 88. A more complete description of these curves and their derivation can be found in "Theoretical and Experimental Investigation of Microwave Moisture Measurement of Materials" by A. Greenwald, FAN, Uzbekistan, 1982.

FIG. 4A shows a graph of a phase region curve 90 as mentioned above. Phase region curve 90 is an empirical curve of the attenuation of antenna signal 38 on the X-axis, and the phase region on the Y-axis. As an example, if the attenuation is equal to $A_1$, phase region curve 90 shows that the phase region lies between 0 and 2p. Different phase region curves must be determined for each material and type of module 10.

In order to use this curve, the attenuation and phase shift of antenna signal 38 are preferably measured as module 10 is conveyed between source antenna 30 and receiving antenna 36. For example, a first measurement could be made before the leading edge of module 10 enters the region between source antenna 30 and receiving antenna 36, a second measurement could be made as the leading edge of module 10 enters that region, and a third measurement could be made when module 10 is aligned between source antenna 30 and receiving antenna 36. The relationship between these multiple measurements and the phase regions is shown in FIG. 4B. At the top is a diagram of module 10 being conveyed between source antenna 30 and receiving antenna 36. At the bottom is a graph of the relationship between the increasing attenuation as module 10 becomes aligned between source antenna 30 and receiving antenna 36, and the phase shift, which is based upon empirical phase region curve 90 of FIG. 4A. As the phase shift cycles between $0-2\pi$ while module 10 is conveyed between source antenna 30 and receiving antenna 36, the number of cycles can be counted and the phase region can be determined.

Figure 5A:
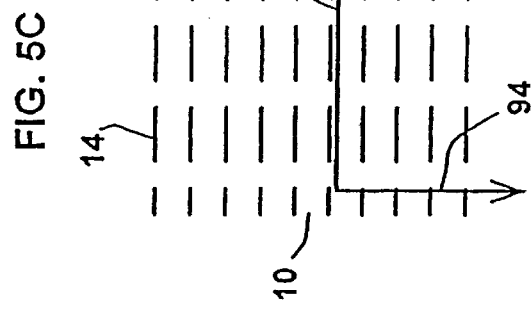
FIGS. 5A–5F illustrate the relationship between the direction of the electrical field of the source beam relative to the module and the attenuation and phase shift of the antenna signal.
Figure 5B:
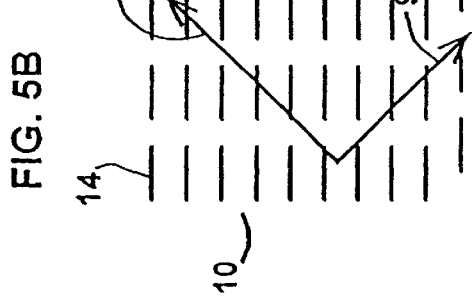
Figure 5C:
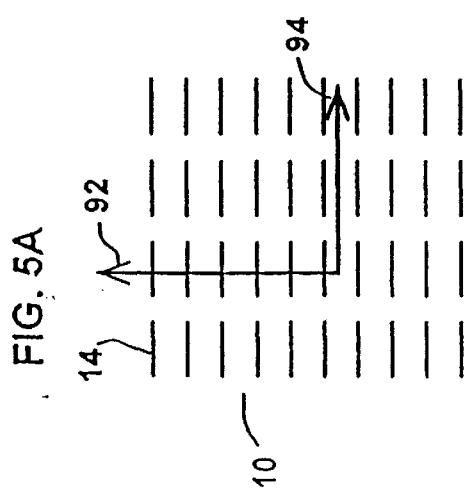
Figure 5D:
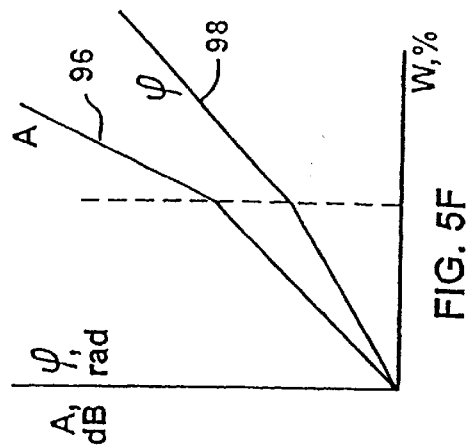
Figure 5E:
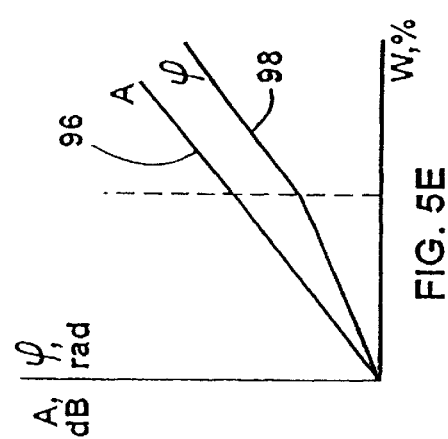
Figure 5F:
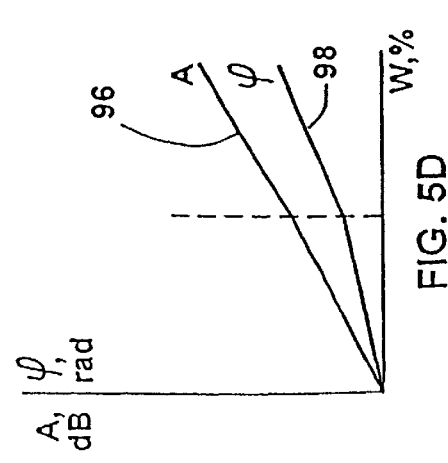

FIGS. 5A–5F illustrate the relationship between the direction of the electric field density of the source beam relative to the module and the attenuation and phase shift of the antenna signal. FIG. 5A shows an electric field density 92 and a magnetic field density 94. Electric field density 92 is perpendicular to layers 14 of module 10. In FIG. 5B, electric field density 92 has been rotated by about 45 degrees. In FIG. 5C, electric field density 92 has been rotated by about 90 degrees, relative to FIG. 5A. Now electric field density 92 is parallel to layers 14 of module 10. FIGS. 5D–5F show the effect of these shifts in the direction of electric field density 92 on attenuation 96 and phase shift 98 of antenna signal 38. In FIG. 5D, both attenuation 96 and phase shift 98 of antenna signal 38 are at substantially a minimum level, because electrical field density 92 is perpendicular to layers 14, as shown in FIG. 5A. In FIG. 5E, both attenuation 96 and phase shift 98 of antenna signal 38 have increased, due to the rotation of electric field density 92 as shown in FIG. 5B. Finally, in FIG. 5F, both attenuation 96 and phase shift 98 of antenna signal 38 are at substantially a maximum level, because electric field density 92 is parallel to layers 14, as shown in FIG. 5C.

Figure 6:
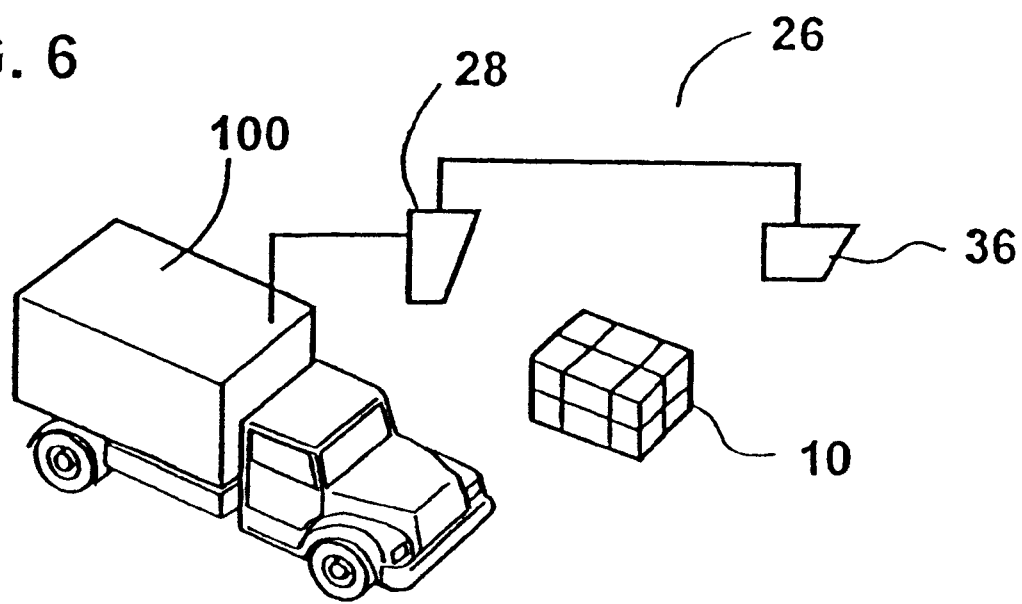
FIG. 6 illustrates a truck for conveying the device of FIG. 2.

Optionally, device 26 can be mounted on a truck 100, as shown in FIG. 6. Microwave radiation source 28 and receiving antenna 36 are both mounted on truck 100. Truck 100 then moves past module 10, so that module 10 passes between microwave radiation source 28 and receiving antenna 36. In this manner, a plurality of moisture measurements of module 10 can be made and averaged, as described above.

Figure 7A:
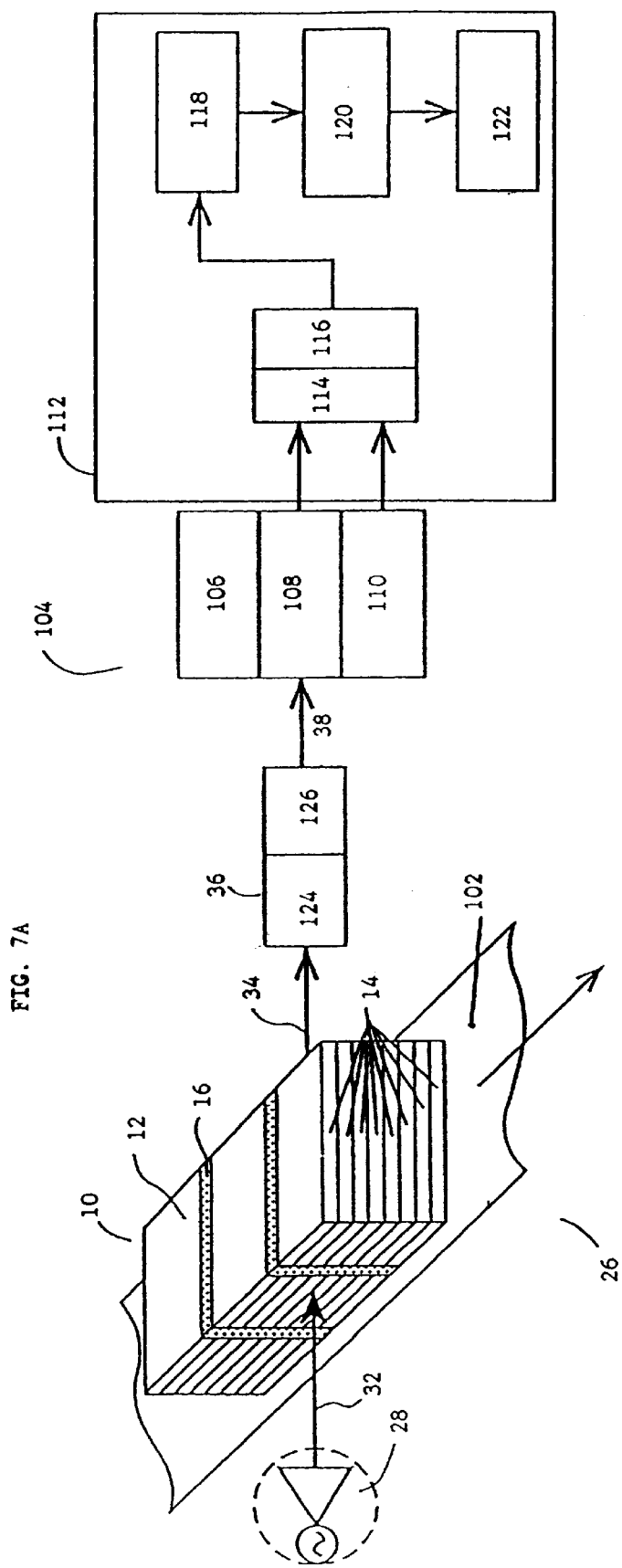
FIGS. 7A–7C illustrate another embodiment of the present invention.
Figure 7B:
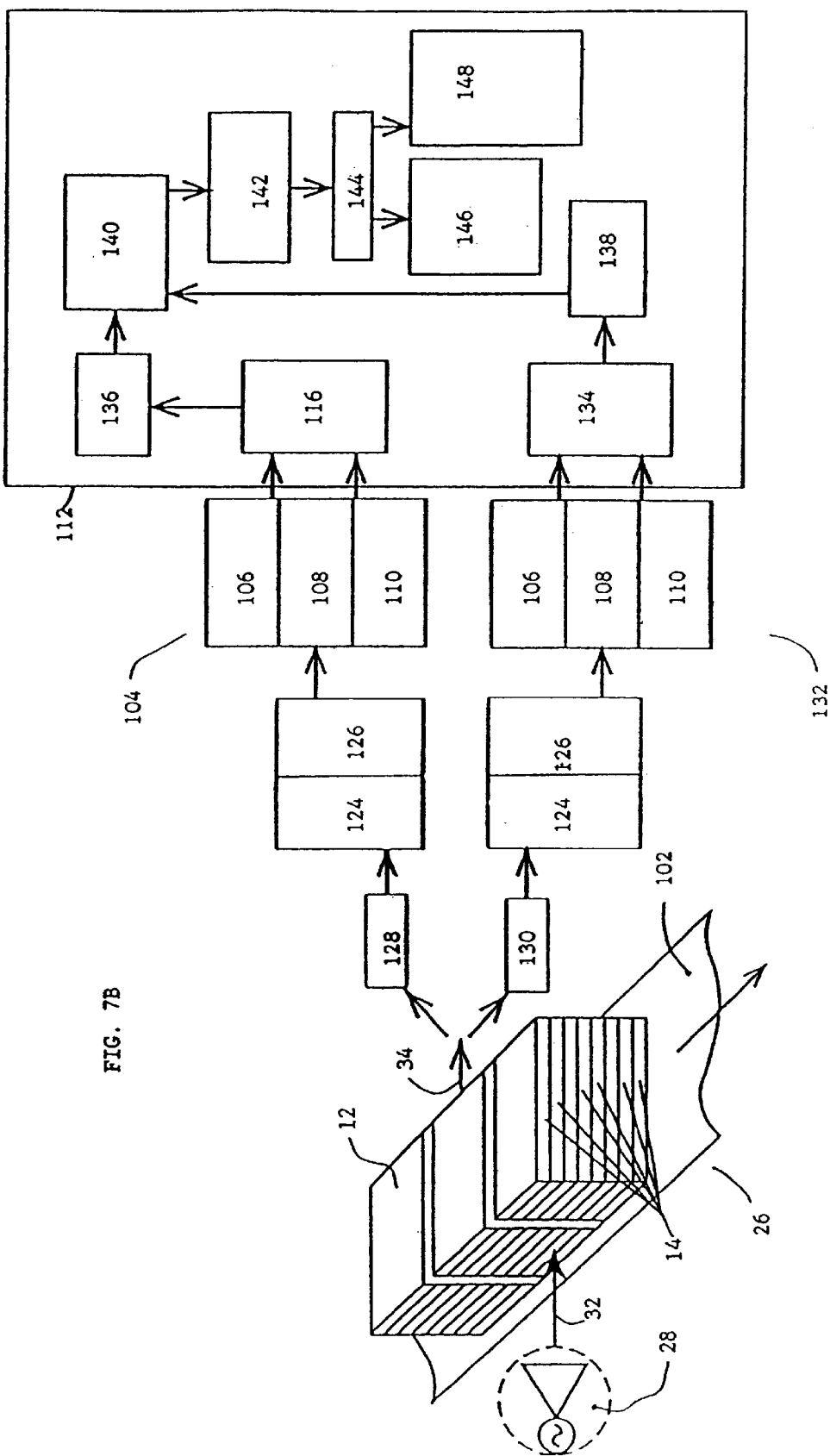
Figure 7C:
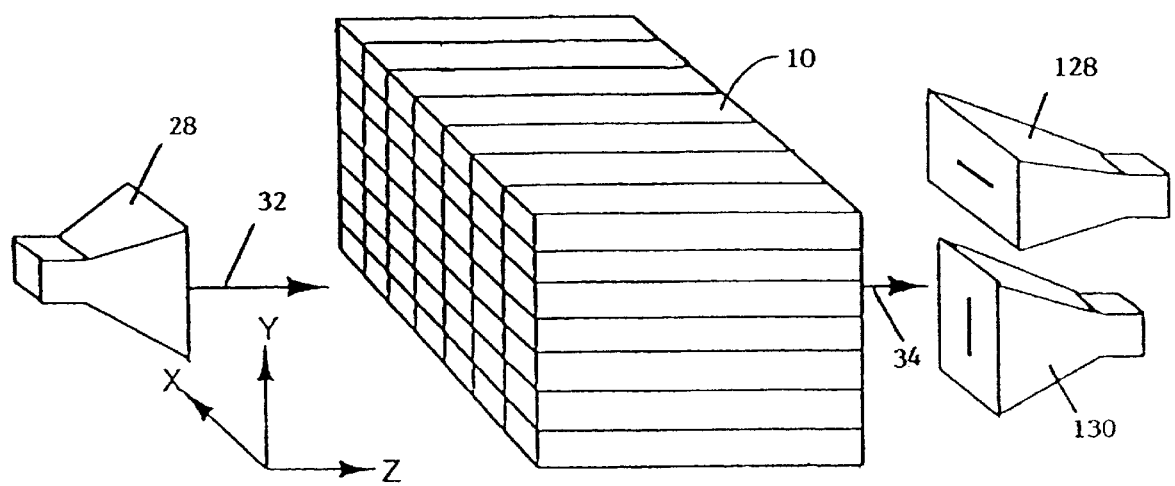

FIGS. 7A–7C illustrate another embodiment of the present invention. FIG. 7A is a schematic illustration of another embodiment of device 26, similar to the one shown in FIG. 2, except that receiving antenna 36 is preferably a circularly polarized antenna. Furthermore, a conveyor 102, such as a conveyor belt, moves module 10, shown here as bale 12, between source of microwave radiation 28 and receiving antenna 36, such that source beam 32 passes through a portion of bale 12, and exits bale 12 as an exit beam 34. Since conveyor 102 is moving module 10, source beam 32 can pass through a plurality of portions of bale 12. Thus, if there are i such portions along bale 12, i moisture measurements can be made. Exit beam 34 is received by receiving antenna 36, which then produces an antenna signal 38.

In this embodiment, antenna signal 38 is then examined by a bale alignment determiner 104. Bale alignment determiner 104 then determines the alignment of bale 12 relative to source beam 32 and receiving antenna 36. Bale alignment determiner 104 includes a leading edge transition determiner 106, an interval timer 108 and a trailing edge transition determiner 110. Leading edge transition determiner 106 detects when a leading edge of bale 12 has passed radiation source 28, and produces a leading edge transition signal. Interval timer 108 receives the leading edge transition signal and produces an alignment signal, such that alignment signal is produced when bale 12 is correctly aligned between microwave radiation source 28 and receiving antenna 36.

Trailing edge transition determiner 110 determines when the trailing edge of bale 12 passes microwave radiation source 28, and produces a trailing edge transition signal.

A moisture determiner 112 then determines the moisture content of bale 12 from the alignment signal. Moisture determiner 112 includes a background moisture content measurer 114, which measures the background moisture content of antenna signal 38 after receiving the trailing edge transition signal. This background moisture content includes both the ambient moisture content, from source beam 32 passing through the air, and artifacts caused by device 26 itself, such as misalignment of source beam 32 relative to bale 12 and movement of receiving antenna 36 from the correct position relative to bale 12. Moisture determiner 112 also includes a filter 116 for producing a corrected signal by removing the background moisture content from the alignment signal.

Preferably, moisture determiner 112 also includes a tie bar suppressor 118. If source beam 32 contacts a tie bar 16 as source beam 32 goes through bale 12, antenna signal 38 can be affected, potentially resulting in an incorrect moisture measurement. Tie bar suppressor 118 removes any such effects from the corrected signal, and produces a further corrected signal. Preferably, this corrected signal then goes to a normalizer 120. Normalizer 120 compensates for effects caused by temperature, mass and length of bale 12, thus normalizing the corrected signal. Such normalization is performed by the following equations:

$W_i$=the $i^{th}$ moisture measurement in the channel, $W_0$=the nominal mass of the bale 250 Kg, $W_0$=the actual measured mass of the bale, $T_0$=the base temperature of the tobacco material (35° C.) and $T_c$=the temperature of the tobacco material in the current slice, $\alpha$=empirical factor compensating for the temperature of the material, it may be shown that $$W'_c = \frac{T_o - T_c}{\alpha} + W_i$$

$$W''_i = W'_i \left(\frac{W_o}{W_c}\right)$$

$$W'''_i = W''_i F(\text{size, shape})$$

The function of (size, shape) is an empirically determined function for f compensating for the size and shape of the tobacco material, for example as a bale.

Finally, the normalized signal preferably goes to a mean moisture unit 122, which determines the moisture content of bale 12. Preferably, mean moisture unit 122 averages the moisture content of bale 12 over all i measurements of i portions of bale 12.

Receiving antenna 36 can optionally include an amplitude determiner 124 and an attenuation determiner 126. Amplitude determiner 124 determines an amplitude of exit beam 34. Attenuation determiner 126 then produces an attenuated signal, by determining an attenuation of exit beam 34 from the amplitude of exit beam 34. The attenuated antenna signal is then processed in a similar fashion as antenna signal 38.

In the preferred embodiment shown in FIG. 7B, source beam 32 is circularly polarized, and exit beam 34 has two mutually orthogonal components. One of these components is in the direction of the X-axis, and one component is in the direction of the Y-axis. For convenience, FIG. 7C shows a partial illustration of device 26 according to FIG. 7B, with X-, Y- and Z-axes illustrated.

Referring back to FIG. 7B, each component is received by one of two linearly polarized microwave receiving antennas 128 and 130, respectively, Each mutually orthogonal component is separately processed, similar to the above description in FIG. 7A, so that there are two bale alignment determiners 104 and 132. Moisture determiner 112 has two filters 116 and 134 for removing the background moisture component and producing a corrected signal. Preferably, two digital samplers 136 and 138 then produce a digitized signal from each component of the corrected signal. There is also preferably a component moisture computer 140 which then computes a moisture content of each mutually orthogonal component of the digitized signal.

Preferably, moisture determiner 112 also has a ratio determination unit 142 for determining a ratio of each of the moisture contents produced by component moisture computer 140, according to the following equations:

$$W_{i_{x(meas)}} = W_{i_x}\cos\beta + W_{i_y}\sin\beta$$

$$W_{i_{y(meas)}} = W_{i_y}\sin\beta + W_{i_y}\cos\beta$$

$$K = \frac{W_{i_x}}{W_{i_y}}$$

where:

$W_{i_{x(meas)}}$=measured moisture content in the X direction for the $i^{th}$ area, $W_{i_{y(meas)}}$=measured moisture content in the Y direction for the $i^{th}$ area, $W_{i_x}$=maximum moisture content of the $i^{th}$ area in the X-direction, $W_{i_y}$=maximum moisture content of the $i^{th}$ area in the Y-direction, $\beta$=the angle of inclination of the layers to the X-direction, K=the ratio of the maximum moisture values in the X and Y directions, and $a_i$=the measured ratio $W_{i_{x(meas)}}:W_{i_{y(meas)}}$ A comparator 144 then compares the ratio with the predetermined constant K, which is obtained when layers in bale 12 are substantially parallel. If the ratio is substantially equal to K, a parallel layer moisture determiner 146 determines the moisture content of bale 12. Otherwise, a non-parallel layer moisture determiner 148 determines the moisture content of bale 12 when the ratio is substantially not equal to the predetermined constant K.

Non-parallel layer moisture determiner 148 preferably determines the moisture content of bale 12 by using an empirical function $$W = W_y + 3.2 \times 10^{-2} \frac{(\gamma - 1)}{K}$$

where W is the moisture content of the signal, $W_y$ is the moisture content of one of the mutually orthogonal components which passed through bale 12 in a direction normal to layers, y is the ratio, and K is the predetermined constant.

Figure 8:
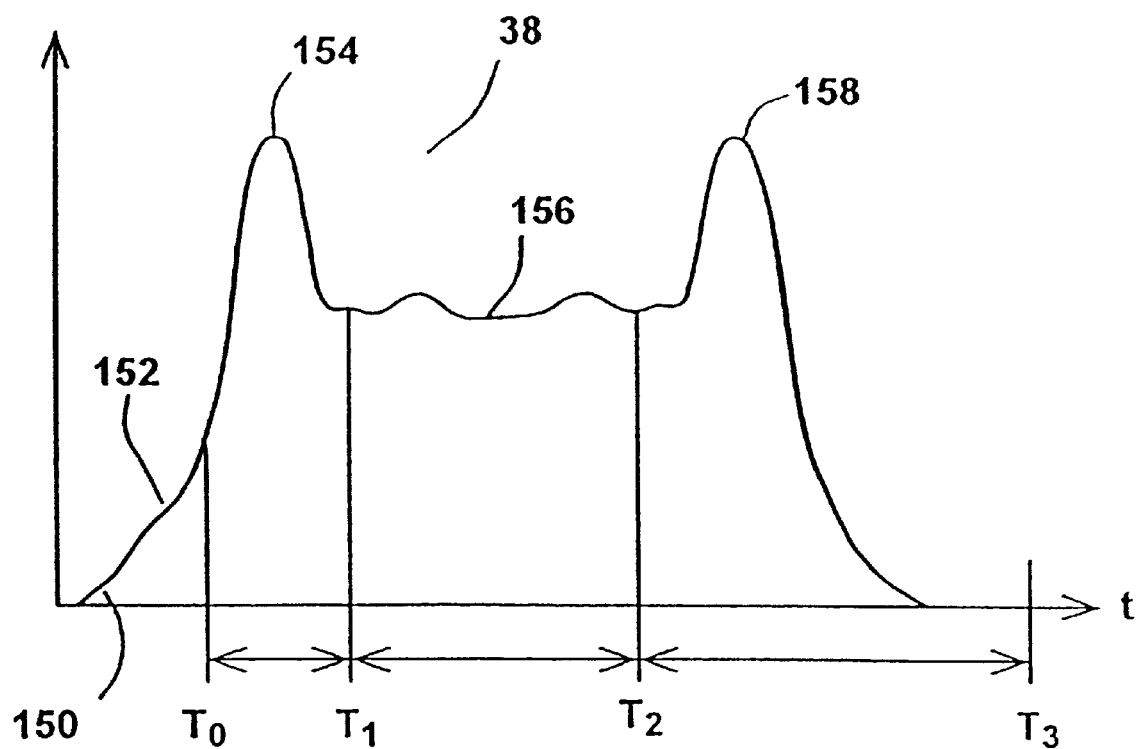
FIG. 8 illustrates the behavior of the antenna signal of the embodiment of FIGS. 7A and 7B.

FIG. 8 illustrates the behavior of the antenna signal of the embodiment of FIGS. 7A and 7B. Antenna signal 38 starts at a generally low background level 150 which climbs to an initial higher level 152 at a time $T_0$ when bale 12 (not shown) enters the region between microwave radiation source 28 (not shown) and receiving antenna 36 (not shown). Antenna signal 38 then reaches a first artifactual peak 154 during time interval $T_1$, due to edge transition effects caused by the leading edge of bale 12 passing between microwave radiation source 28 (not shown) and receiving antenna 36 (not shown). During this time, a first portion of source beam 32 passes through bale 12 (not shown), and a second portion does not, causing these edge transition effects.

Once bale 12 (not shown) is correctly aligned between microwave radiation source 28 (not shown) and receiving antenna 36 (not shown), for example as in FIGS. 7A and 7B, antenna signal 38 goes to a steady level 156 during time interval $T_2$ and remains substantially constant during this time interval, except for fluctuations due to local inequalities in the moisture content and structure of bale 12. During time interval $T_2$, the alignment signal is produced, and all moisture measurements of bale 12 are made. At time $T_3$, the trailing edge of bale 12 (not shown) starts to move past microwave radiation source 28 (not shown) and receiving antenna 36 (not shown), causing a second artifactual peak 158, again due to edge transition effects caused by the trailing edge of bale 12.

Figure 9:
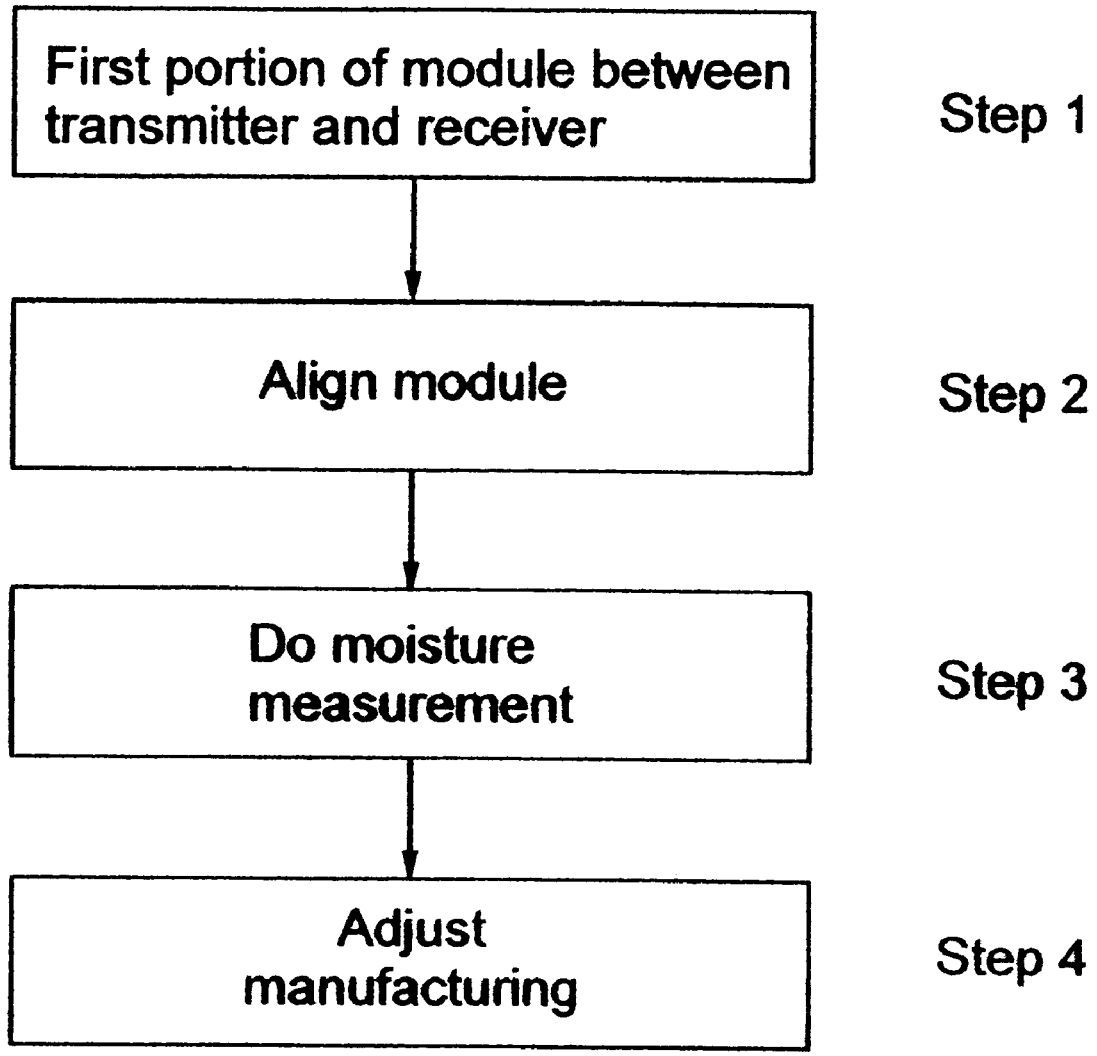
FIG. 9 is a flow chart of another method of calculating the moisture content of the tobacco material.

FIG. 9 is a block diagram of an exemplary method for determining the moisture content of tobacco according to the present invention. The method of the present invention can be used with any of the embodiments of the device as described herein, as well as with any of the described methods for performing the calculations of the moisture content of the material.

In step one, a first portion of the module of tobacco moves between a source of microwave radiation and a receiving antenna. In step two, once the bale is correctly aligned between the source of microwave radiation and the receiving antenna, the alignment signal is produced. In step three, at least one, and preferably a plurality, of moisture measurements are made substantially as described for FIGS. 2–7, 9 or 10. More preferably, in step three the effect of the tobacco material itself is removed from the measured moisture content in order to more accurately determine the moisture content of the material. Most preferably, such an effect is determined empirically, as described in greater detail below.

In step four, the manufacturing process of the tobacco product, such as cigarettes, pouch tobacco or chewing tobacco, is preferably adjusted according to the moisture content of the material. For example, if the moisture content of the tobacco material is above a predetermined level, preferably the stored tobacco is processed more quickly, such that the period of storage is reduced. Alternatively and preferably, the manufacturing process is adjusted according to the moisture content of the tobacco material such that the finished tobacco product has a moisture content within a predetermined, acceptable range, which is approximately 12–18% for the loose leaves, and 11–13% after processing.

Figure 10:
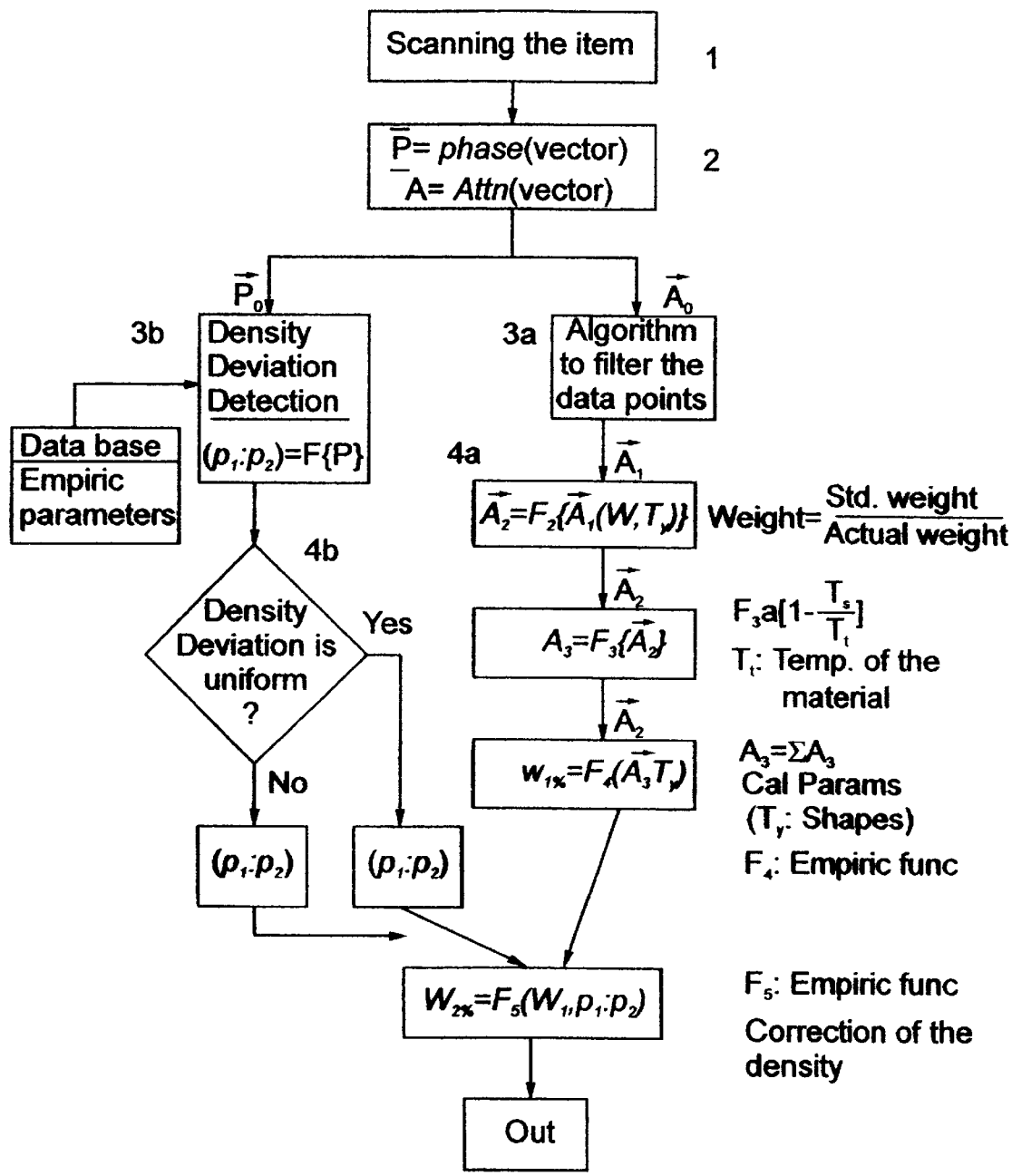
FIG. 10 is a flow chart of anther method for calculating the moisture content of the tobacco material.

FIG. 10 shows a flow chart of the calculations for determining the moisture content and the internal structure of the tobacco module, particularly for bales of tobacco. The attenuation if used to determine the raw moisture content of the material, while the phase shift is used to determine the internal structure of the material. Both the attenuation and the phase shift are preferably used in combination with empirically determined correction factors to calculate the final moisture content of the material.

The first step in the flow chart is the scanning of the material, which can be performed using the device essentially as described in any of the embodiments above. The material is scanned by transmitting a plurality of microwaves through the bale so that they pass through the bale and are received on the other side. From this scanning step, the phase shift and the attentuation are calculated, as shown in step 2. The flow chart now branches into two parts. The right branch shows the steps used in calculating the raw moisture content of the material, while the left branch shows the steps for the determination of the internal structure of the material. For clarity, steps in the right (moisture content) branch will have the letter "a" appended; e.g., "3a", "4a", etc. Steps in the left (internal structure) branch will have the letter "b" appended; e.g., "3b", "4b", etc.

Following the right branch, in step 3a an algorithm is used to filter the data points obtained for the attenuation. Each time a measurement of the attentuation is made as described above in FIG. 2, a data point is obtained. These data points must be filtered, since otherwise artefactual data could be obtained.

Once the data has been filtered, the attenuation is corrected for the effect of the weight of the material and the bale, as shown in step 4a. This correction is preferably performed by compensating the attenuation with the ratio of a standard weight to the actual weight, for example by multiplication when the material is tobacco, and produces a weight-corrected attenuation value. Next, in step 5a, the weight-corrected attenuation value is preferably corrected for temperature, to produce a temperature-corrected attenuation value. The correction is performed by adding the weight-corrected attenuation value to the factor a(1–Ts/Te), where Ts is the standard temperature, and Te is the measured temperature of the material, in order to produce the temperature-corrected attenuation value. The temperature of the material is preferably measured by inserting a temperature probe into the bale, for example. The value of a is empirically determined according to the type of material. More preferably, the temperature is substantially continuously monitored by the temperature sensor, so that each measurement of the attenuation can be corrected with the temperature value taken as the transmission of microwaves was made. The temperature-corrected attenuation value thus is compensated for the effect of measurements at different temperatures.

In step 6a, the complete set of all temperature-corrected attenuation values from a single slice of material is used to calculate a raw moisture value for that slice. This calculation is performed according to a function which can be a linear integration of all the temperature-corrected attenuation values or else a polynomial, depending upon such empirical factors as the type of tobacco material being measured, the shape and structure of the bale itself. In any case, these empirical factors are included in the calculation, so that their effects on the measurement can be compensated for. For example, these factors include but are not limited to the type of tobacco leaf, and the structure of the tobacco such as loose leaves or a type of bale.

This raw moisture value will be used in the determination of the final moisture value for the slice of material. However, the final moisture value cannot be determined without knowing the density of material, which is calculated as shown in the left branch of the flow chart.

Turning back now to the left branch, which includes steps for calculating the density of the material, the density is calculated from the phase shift, in accordance with empirical information from a database. The empirical information includes the type of tobacco material and the structure of the bale itself.

Additionally, the database preferably contains "fuzzy descriptors" which are used to find the correct phase region and to determine the proper relationship between measured phase shift values and calculated density values. These "fuzzy descriptors" are obtained by collecting phase shift data from an analysis of test modules of tobacco having known features, and then comparing the calculated density values with the true, known density values of the test module. From this analysis of the test module, the proper correlation between the measured phase shift values and the calculated density values can be determined. Since this correlation depends both upon the structure of the test module, and upon the type of tobacco material or materials from which the test module is constructed, such an analysis must be performed for substantially every structure of module and type of tobacco material in order to obtain these essentially empirical correlations.

In step 4b, any deviation of the measured density of the slice of material from the previous measurement of the density of the previous slice is determined. Such deviations are important because they reveal irregularities in the internal structure of the material.

In step 5b, the true density of material is calculated in one of two different ways, depending upon deviations in the calculated density when comparisons are made between two or more slices. In the first method, the deviation in the calculated densities between a plurality of slices is relatively small, such that a single density value can be used for all subsequent calculations. Alternatively, the deviation between the calculated densities of a plurality of slices is relatively large, such that a plurality of density values, and preferably all density values, are used for the subsequent calculations.

Finally, in step 7, the true density value or values, and the raw moisture value, which is calculated in step 6a, are combined to determine the true moisture value. The equation for calculating the true moisture value includes both the true density and any deviations in the calculated density within the slice, as well as an empirically determined correlation factor. The correlation factor depends upon the type of tobacco material and the structure of the module of material, and was empirically determined through prior experimentation. In addition, preferably substantially continuous feedback of previous moisture measurements is also correlated with the current moisture measurement as a correction function. The true moisture value is then output, for example by displaying on a display unit which could include a video screen, or by other devices for displaying the information. Preferably, any deviations in the internal structure of the material which were found by comparison of the measured phase shifts are also displayed, since such information can be very important to the manufacturer or processor of the material.

Figure 11A:
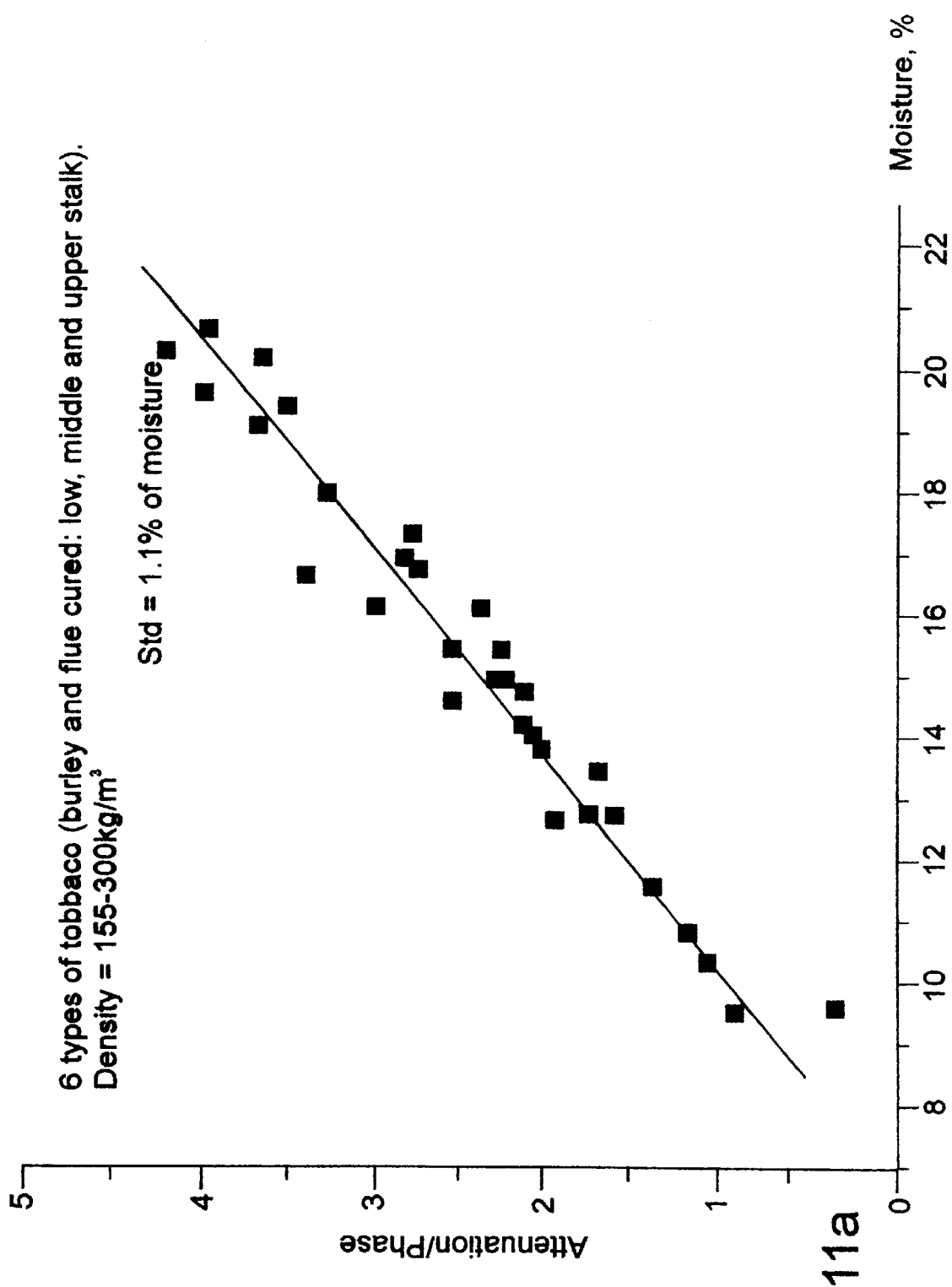
FIGS. 11A–11D show illustrative experimental results using the method of the present invention.

FIGS. 11A–11D show various types of moisture measurements for tobacco which were performed according to the present invention. FIG. 11A is a graph of the true moisture content as a weight percentage (x-axis) against the ratio of the measured attenuation to the measured phase, which represents density (y-axis). Six types of tobacco were measured (burley and flue cured, with lower, middle and upper stalk for each) in various structures. The density varied from 155 kg to 300 kg per cubic meter. As shown, a very good correlation was obtained between the true moisture content and the measured attenuation and phase ratio. The standard deviation was only 0.4% of the true moisture content. Thus, the method of the present invention was clearly able to accurately measure the moisture content of the tobacco.

Figure 11B:
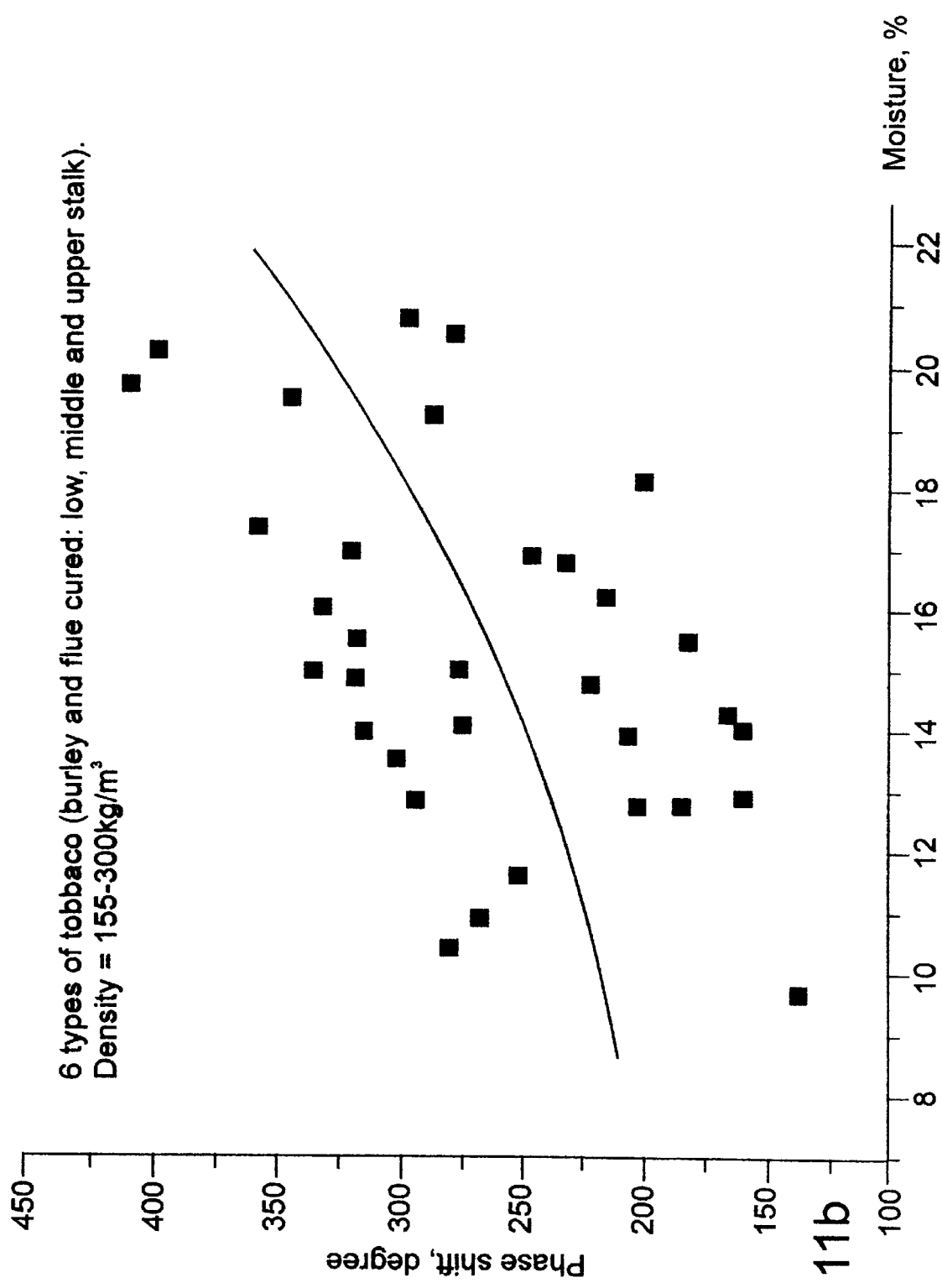
Figure 11C:
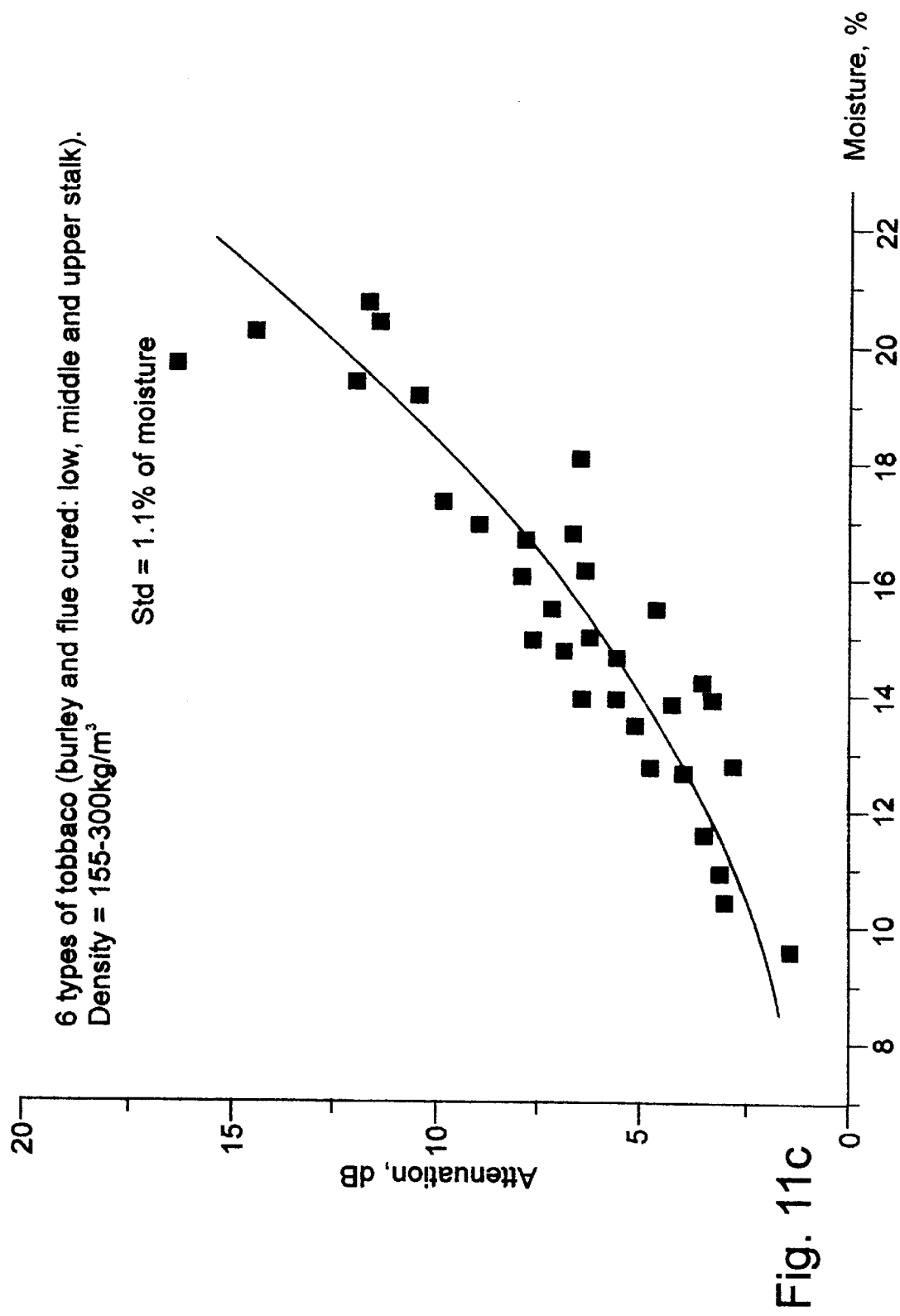

FIG. 11B shows the results of the phase shift measurements alone (y-axis) against the true moisture content of the material for the measurements described for FIG. 11A. As can be seen, without any correction for the density deviation or correlation with the attenuation, the values of phase shift are not as correlated with the true moisture content. The spread of the phase shift values compared to the true moisture content is caused by the significant deviations of the density of the material, which included packages of tobacco. Similarly, for FIG. 11C, the measured attenuation values (in dB) alone were also spread when correlated with the true moisture content, again caused by the density deviation of the packages of tobacco. The standard deviation was 1.1% of the true moisture content, higher than the 0.4% deviation obtained when the measured phase shift and attenuation values were correlated as shown in FIG. 11A. Thus, clearly the determination of the moisture content of the material with both the measured phase shift and attenuation, according to the method of the present invention, is able to produce measured moisture content which is much more closely correlated to the true moisture content of the material.

Figure 11D:
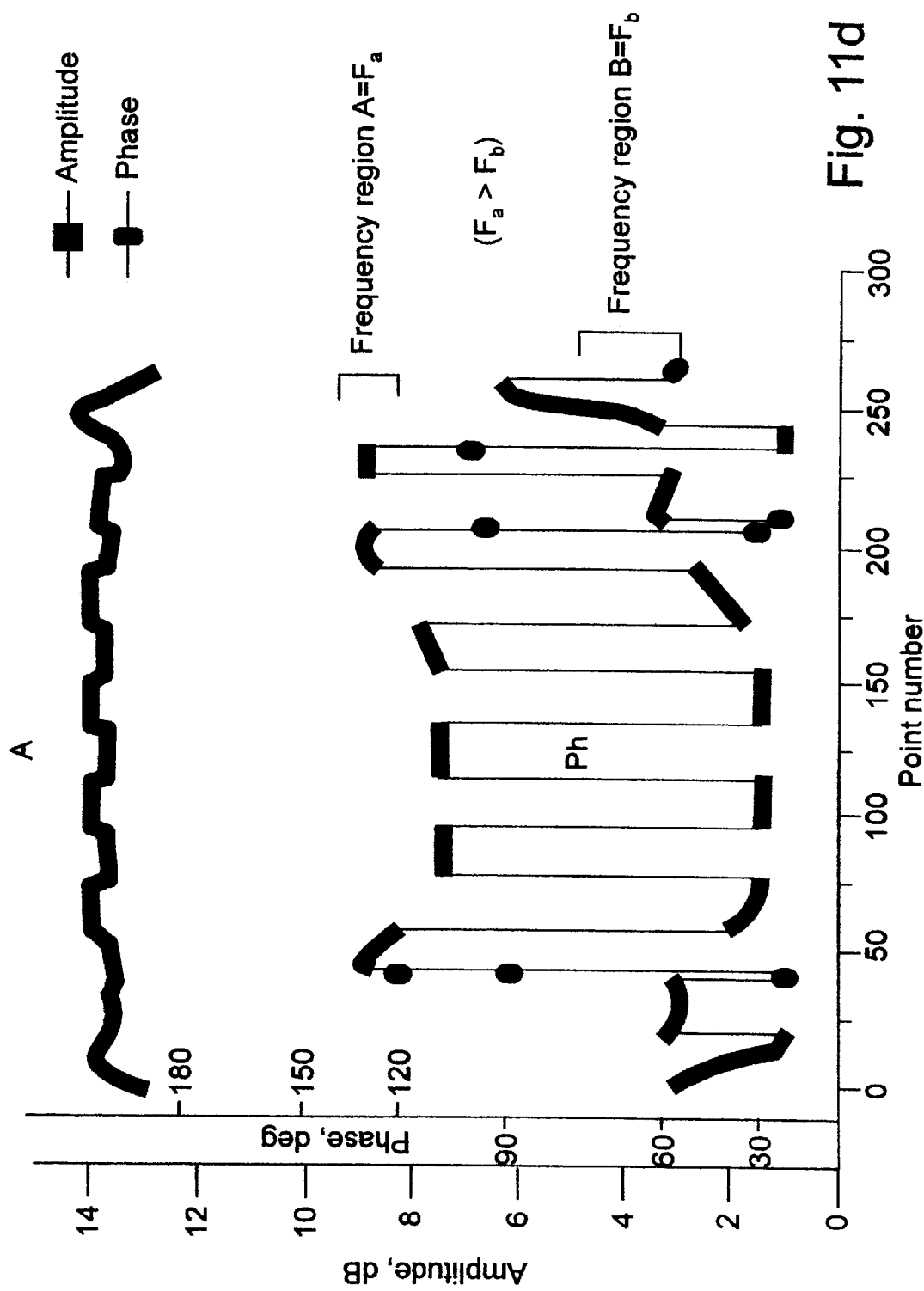
Figure 1A:
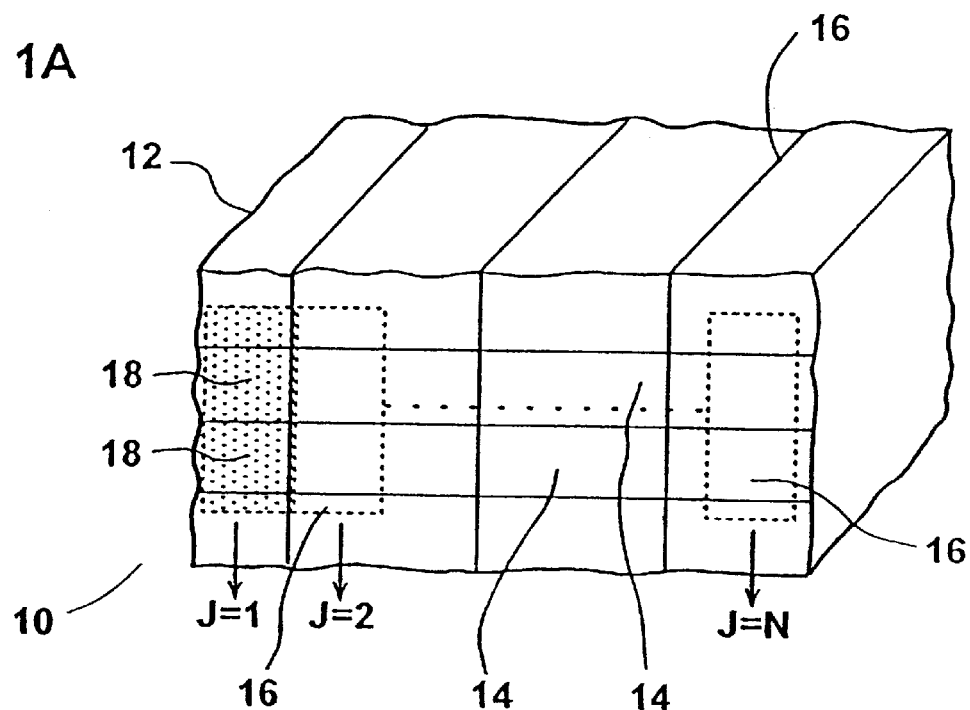
Figure 1B:
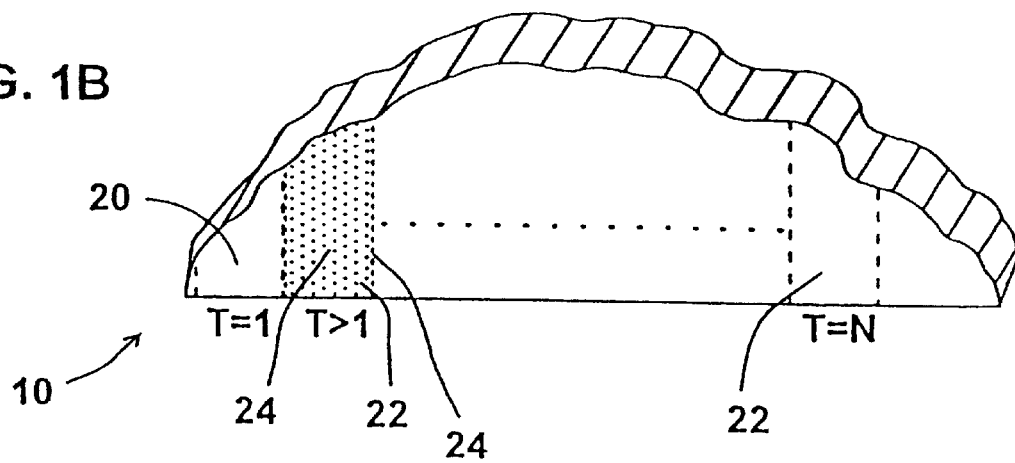

FIG. 11D shows the measured amplitude or phase of the tobacco material, performed according to the method of the present invention (y-axis) for each data point obtained (x-axis). The measurements were performed with two frequencies of microwaves, Fa and Fb, in which Fa>Fb. The device and method of operation are described with regard to FIG. 12 below. Briefly, both the attenuation and phase shift are determined at the two frequencies of microwave radiation, as shown. A table of the measured values is given below.

Table of measured values

| Data point | Attenuation | Phase shift |
|---|---|---|
| Data Region $F_1$ = 3.24 GHz | | |
| 1 | 13.62 | 34.77 |
| 2 | 13.62 | 34.83 |
| 3 | 13.62 | 34.73 |
| 4 | 13.62 | 34.64 |
| 5 | 13.62 | 34.77 |
| 6 | 13.62 | 34.86 |
| 7 | 13.62 | 34.7 |
| 8 | 13.62 | 34.77 |
| 9 | 13.62 | 34.86 |
| 10 | 13.62 | 34.73 |
| Data Region $F_2$ = 3.45 GHz | | |
| 11 | 13.88 | 115.69 |
| 12 | 13.87 | 115.53 |
| 13 | 13.88 | 115.63 |
| 14 | 13.88 | 115.63 |
| 15 | 13.87 | 115.53 |
| 16 | 13.88 | 115.53 |
| 17 | 13.87 | 115.59 |

These values are then used to calculate the moisture content of the material, by first correcting the phase shift according to the following equation:

$$Ph_{F_1} = \frac{\Delta Ph(F_2) - \Delta Ph(F_1)}{F_2 - F_1} F_1$$

For this equation, $F_1$ is the first frequency and $F_2$ is the second frequency; $Ph_{F_1}$ is the measured phase shift for the first frequency $F_1$; and $\Delta Ph(F_1)$ and $\Delta Ph(F_2)$ are the phase shifts for $F_1$ and $F_2$, respectively. Taking exemplary values from the above Table, the equation was solved as follows:

$$Ph_{F1} = \frac{115.6 - 34.7}{3.45 - 3.24} 3.24 = 1248$$

Next, the true phase shift was determined as follows.

$$(Ph_{F_1} \bmod(360) * 360) + \Delta Ph(F_1) = P_{true}$$

Briefly, first, the measured phase shift $Ph_{F_1}$ (1248 degrees) was divided by 360 to obtain 3.47. The integral portion of 3.47 was taken to obtain 3, which was then multiplied by 360 to get 1080, after which $\Delta Ph(F_1)$ was added to obtain the true phase shift ($P_{true}$), or 1114 degrees. Although these equations are shown in relation to $F_1$, in fact substantially any such frequency could be used in order to obtain more information and to minimize the statistical error.

Next, A(dB)/Ph(degrees)=13.62 dB/1114 degrees=0.012. From the previous graph of the ratio of the attenuation to the phase shift (FIG. 11A), the ratio value of 0.012 yielded a moisture content of 11.2 percent.

FIG. 12 shows a schematic diagram of another preferred embodiment of the present invention, in which the system described previously has been adjusted to permit transmission of more than one frequency of microwave radiation. It should be noted that this preferred embodiment can be used to determine the moisture content of tobacco material having substantially any structure as encompassed by the term "module", including bales, bales and/or any other bulk of material. Thus, a module can have a substantially irregular structure with variable density.

A multiple-frequency system 160 has a multiple-frequency transmitter 170 for sequentially transmitting microwave radiation at a plurality of frequencies. The frequency to be transmitted is selected by a frequency controller 172. Transmitter 170 then causes a transmitting antenna 172 to transmit microwave radiation at the desired frequency. The transmitted microwave radiation then passes through a module or bale of material (not shown) and is received by a receiving antenna 174. Receiving antenna 174 sends a signal to a signal receiver 176. Signal receiver 176 is preferably a hetrodyne receiver. Substantially simultaneously, a reference signal is sent from transmitter 170 to a reference receiver 178, which is also preferably a hetrodyne receiver. Signal receiver 176 sends a measurement signal (labelled as "I.F.1") to a detector 180, while reference receiver 178 sends a reference signal (labelled as "I.F.2") to detector 180. Detector 180 uses the reference signal to determine the correct attenuation of the measurement signal, and then passes both signals to a phase detector 182, which determines the correct phase shift for the measurement signal.

The gross phase shift difference between two phase shifts measured after microwave radiation of two different frequencies has been transmitted through the material can be described as follows.

$$\Delta P(\text{gross}) = F_2/(F_2-F_1)*(P_2-P_1)$$

The final phase shift difference is:

$$\Delta P(\text{final}) = Pi + Pg \bmod (2\tau.)$$

Thus, the gross phase shift difference is obtained by sequentially transmitting microwave radiation of at least two different frequencies, and "hopping" or alternating at least between these two frequencies at each point in the material.

The equations which describe the phase shift and attenuation are as follows.

1. $\lambda = C/F$; $l$ = (wave length of radiation);

$\varepsilon'$ = (dielectric constant of material)

2. $P_1 = \dfrac{2\pi}{\lambda_1}\sqrt{\varepsilon'}\, l$;

3. $P_2 = \dfrac{2\pi}{\lambda_2}\sqrt{\varepsilon'}\, l$;

4. $P_1 = KF_1$; $P_2 = KF_2$; $K = \dfrac{2\pi}{C}\sqrt{\varepsilon'}\, l$;

$P_1 - P_2 = \Delta P = K(F_1 - F_2)$;

5. $P_1 = Ph_{(t)}(F_1)$; $P_2 = Ph_{(t)}(F_2)$;

-continued

6. $K = \dfrac{P_1 - P_2}{F_1 - F_2}$; $(F_1 > F_2)$

7. $Pg$ = (phase including $n\pi$ term) = $K \cdot F_i$ ($i$ is 1 or 2)

8. Corrected Phase-shift = $(Pg \bmod (360))*360 + P_i$ ($i$ is 1 or 2); $n = (Pg - n2\pi > 0)$ Note that F is the frequency of the microwave radiation; l is the wavelength; $\varepsilon'$ is the dielectric constant of the bulk of material; $P_1$ is the phase deviation for microwave radiation at frequency $F_1$; $P_2$ is the phase deviation for microwave radiation at frequency $F_2$; $K(F_1-F_2)$ is the difference between the phase deviation of the radiation at frequencies $F_1$ and $F_2$; $P_{h(t)}$ is the true phase shift, such that the measured phase shift, $P_1$, is a function of the true phase shift and of the frequency $F_1$, for example; Pg is the gross phase shift difference; and n is the largest number which satisfies equation 8 such that Pg-n$\pi$ is greater than 0.

Although these equations both describe the corrected phase shift and can be used for its calculation, the refinements of the calculations must be done according to empirically observed properties of the material itself and effects of the surrounding environment. FIG. 11 shows a flow chart of these empirically-based calculations. In step 1, a plurality of frequencies of microwave radiation are sequentially transmitted through the material in a module. In step 2, the attenuation and the corrected phase shift are calculated for the plurality of frequencies of microwave radiation.

In step 3, an algorithm is performed to filter noise from the calculated values of the attenuation and the corrected phase shift. The attenuation for a frequency $F_{2i}$ can be described as $A_{2i}=a_1A_{1i}+b_1$. Similarly, the phase shift is $P_{i2}=a_2P_{1i}+b_2$. Note that $A_{1i}$ and $P_{1i}$ are the attenuation and phase shift values obtained from the previously measured frequency $F_{1i}$. The values for $a_1$, $a_2$, $b_1$ and $b_2$ are taken from a database, depending upon the particular application and material. For example, one set of values would be required for tobacco in a bale, while another set of values would be required for a loose pile of tobacco leaves. These values are empirically determined based upon empiric measurements of the material concerned. This calculation to filter noise is preferably performed upon all calculated values of the attenuation and the corrected phase shift. In addition, the value of each of the plurality of frequencies is used for these calculations, since the attenuation and phase shift values are also dependent upon the frequency of the microwave radiation.

Preferably, any "edge" measurements, or measurements made when an edge of material was passing through the beam of microwave radiation, are eliminated from any subsequent calculations since these measurements are artefactual. The determination of whether a particular measurement is an "edge" measurement can be made in a number of ways. For example, the location of the module relative to the beam can be determined, such that when an edge of the module is about to pass through the beam, a signal can be sent to the attenuation and phase shift determiners. Alternatively and preferably, the measurement of the attenuation can be plotted, and any artefactually high peaks or low troughs of attenuation can be eliminated, for example by removing any values which are more than two or three standard deviations from the average attenuation. Thus, any artefactual "edge" measurements are preferably eliminated at this stage of the analysis.

In step 4, the density and the moisture content of the material are calculated from the plurality of filtered attenuation and filtered phase shift values, preferably from all of these values. The moisture content of the material is determined from the following equation:

$$W_\% = \sum_{i=1}^{n} W_i * r_i$$

in which $r_i$ is the correlation factor described previously. The term $W_i$ is a function of the attenuation $A_2$ and the phase shift $P_2$ as determined in step 3, as well as of the type and structure of material. The correlation factor is obtained from a database of these values, determined from empiric observation.

The density of the material is then calculated from a statistical function of the sum of the phase shift values, again taken from the database. This function depends upon the characteristics of the material being analyzed, as for the calculation to filter noise described for step 3. Also, the density is a function of both $P_2$ as determined in step 3, and the type and structure of the material. Thus, the necessary information is taken from a database of empirically determined information.

Preferably, at this stage any defects in the material are detected by examining the densities collected for a portion of the material. The defect could include an irregular moisture distribution within the interior of the material, such as an unusually high moisture content within the material, and the presence of a foreign body inside the material, for example.

In step 5, the temperature of the material is preferably compensated for in the determination of the moisture content and density, if necessary. Again, the necessity for step 5 is determined at least partially according to empiric observations.

In step 6, the moisture content and the density of the material is output, for example to a display on a computer screen or by printing onto paper.

The advantages of determining the moisture content and density of each point in a material at more than one frequency of microwave radiation are as follows. First, measuring the attenuation and phase shift at one point in the material but with more than one frequency permits averaging of the values to obtain a more accurate result. Second, the change in the attenuation is linear, so that alterations in the attenuation due to the measurement at different frequencies can be easily calculated. Any remaining differences are then removed by averaging. Third, a good range of frequencies for any particular type or form of material can be selected, rather than relying upon a single frequency. Finally, measurements at the chosen range of frequencies also enable the true phase shift to be determined.

The third point, the ability to choose a good range of frequencies for a particular type or form of material, is particularly important for mixed materials, or materials containing more than one type of substance. For example, tobacco leaves are often mixed with extraneous material such as stems, which affect the measured moisture content of the tobacco leaves themselves. Additionally, this mixture of different types of materials with different properties cause harmonics to appear in the transmitted microwaves. However, the true phase shift can be determined from a linear portion of the curve of phase shift plotted against frequency. Thus, using a plurality of frequencies can simplify the determination of the phase shift for mixed materials.

Optionally and preferably, a frequency range of microwave radiation can be chosen which minimizes reflection of radiation from the material and maximizes transmission of microwave radiation through the material. More preferably, a range of suitable frequencies is chosen from a database before the measurements are made. The choice of a particular range is empirically based on such factors as the type of material and the structure of material. Therefore, tobacco in a bale would require a different range of frequencies than loose tobacco leaves, for example. As the measurements are made, the frequency range can also be selected to reduce or eliminate ambient noise from environmental interference. An example of such interference could be a cellular phone. Preferably, more than one frequency range is examined before selecting a particular range in which to make the measurements, in order to reduce or eliminate this problem.

In addition, preferably adjustments are made to the selected range of frequencies, such that more measurements are made within a smaller range of frequencies which gives the best results. Thus, adjustments to the frequency range made "on the fly" enable the most sensitive and accurate measurements to be made.

While the invention has been described with respect to a limited number of embodiments, it will be appreciated that many variations, modifications and other applications of the invention may be made.

What is claimed is:

1. A method of determining a moisture content of tobacco material, the method comprising the steps of:
   (a) transmitting a plurality of microwaves substantially through at least a portion of the material, such that said microwaves are transmitted microwaves;
   (b) receiving said transmitted microwaves such that said microwaves are received microwaves;
   (c) determining an attenuation from said received microwaves;
   (d) using at least one empirical factor selected from the group consisting of weight of the material, temperature of the material, structure of the material and type of the tobacco material to correct said attenuation, producing a corrected attenuation; and
   (e) calculating the moisture content of the tobacco material from said corrected attenuation.

2. The method of claim 1, wherein the step of determining said attenuation further comprises the step of determining a phase shift from said received microwaves.

3. The method of claim 2, wherein the step of determining said attenuation further comprises the step of:
   (i) repeating steps (a) to (c) for at least a portion of the material on the bale, such that a plurality of phase shifts and a plurality of attentuations are obtained, and such that a plurality of corrected phase shifts are produced according to said plurality of phase shifts.

4. The method of claim 3, further comprising the step of:
   (ii) determining a density of the material from said phase shifts; and
   (iii) calculating a final moisture content of the material from said density and from said raw moisture content.

5. The method of claim 3, wherein the material features an internal structure and an irregularity of said density of said internal structure is calculated by comparing one of said plurality of phase shifts to a previous value of said phase shifts, such that said irregularity is detected if one of said plurality of phase shifts differs from said previous value.

6. The method of claim 5, wherein said irregularity of said density of said internal structure indicates that the material is of more than one type of tobacco.

7. The method of claim 3, wherein a first phase shift is determined for microwave radiation of a first frequency $F_1$, and a second phase shift is determined for microwave radiation of a second frequency $F_2$, said first phase shift being corrected to form a first measured phase shift according to the equation:

$$Ph_{F_1} = \frac{\Delta Ph(F_2) - \Delta Ph(F_1)}{F_2 - F_1} F_1$$

wherein $Ph_{F_1}$ is said measured phase shift for said first frequency $F_1$; and $\Delta Ph(F_1)$ and $\Delta Ph(F_2)$ are said phase shifts for $F_1$ and $F_2$; and wherein a first corrected phase shift is formed according to the following equation:

$$(Ph_{F_1} \mod(360)*360) + \Delta Ph(F_1) = P_{true}$$

such that $P_{true}$ is said first corrected phase shift.

8. The method of claim 7, wherein the moisture content is determined according to a ratio of said attenuation and said corrected phase shift.

9. The method of claim 8, wherein an empirical curve of a relation between said ratio and the moisture content is provided, such that the moisture content is determined according to said ratio by using said empirical curve.

10. The method of claim 1, wherein the tobacco material is contained in a module.

11. The method of claim 10, wherein said at least one empirical factor is a plurality of empirical factors selected from the group consisting of weight of the module, type of the material, structure of the module, location of the module relative to said plurality of microwaves and temperature, and said factors are stored in a database.

12. The method of claim 11, wherein said corrected attenuations and said phase shifts are further corrected by removing attenuations and phase shifts produced after said plurality of microwaves passes through an edge of the module, such that a first portion of said plurality of microwaves passes through said portion of the module and a second portion of said plurality of microwaves substantially does not pass through said portion of the module.

13. The method of claim 1, wherein the step of determining said density includes detecting a defect in the material, said defect being selected from the group consisting of irregular moisture distribution within an interior of the material and presence of a foreign body inside the material.

14. A method for determining a moisture content of tobacco material, the method comprising the steps of:
(a) transmitting a plurality of microwaves substantially through at least a portion of the material, such that said microwaves are transmitted microwaves;
(b) receiving said transmitted microwaves such that said microwaves are received microwaves;
(c) determining an attenuation from said received microwaves;
(d) determining a phase shift from said received microwaves; and
(e) calculating the moisture content of the tobacco material from a ratio of said attenuation and said phase shift.

15. The method of claim 14, wherein the step of calculating the moisture content further comprises the steps of:
(i) providing an empirical curve of a relation between said ratio and the moisture content; and
(ii) determining the moisture content according to said ratio by using said empirical curve.

16. The method of claim 15, wherein the step of determining said attenuation further comprises the step of:
(i) using at least one empirical factor selected from the group consisting of weight of the material, temperature of the material, structure of the material and type of the tobacco material to correct said attenuation, producing a corrected attenuation.

17. The method of claim 16, wherein the step of determining said phase shift further comprises the steps of:
(i) determining a first phase shift for microwave radiation of a first frequency $F_1$;
(ii) determining a second phase shift for microwave radiation of a second frequency $F_2$; and
(iii) correcting said first phase shift to form a first measured phase shift according to the equation:

$$Ph_{F_1} = \frac{\Delta Ph(F_2) - \Delta Ph(F_1)}{F_2 - F_1} F_1$$

wherein $Ph_{F_1}$ is said measured phase shift for said first frequency $F_1$; $\Delta Ph(F_1)$ and $\Delta Ph(F_2)$ are said phase shifts for $F_1$ and $F_2$; and wherein a first corrected phase shift is formed according to the following equation:

$$(Ph_{F_1} \mod(360)*360) + \Delta Ph(F_1) = P_{true}$$

such that $P_{true}$ is said first corrected phase shift.

18. A method for determining a moisture content of tobacco material, the method comprising the steps of:
(a) transmitting a plurality of microwaves of a plurality of frequencies substantially through a portion of the material, said microwaves of each of said plurality of frequencies being transmitted sequentially such that said microwaves are transmitted microwaves of a particular frequency;
(b) receiving said transmitted microwaves of said particular frequency such that said microwaves are received microwaves of said particular frequency and such that said transmitted microwaves from said plurality of frequencies are received;
(c) determining an attenuation from said received microwaves of each of said particular frequencies, such that a plurality of attenuations is determined;
(d) determining a phase shift from said received microwaves of each of said particular frequencies, such that a plurality of phase shifts is determined;
(e) correcting each of said plurality of phase shifts according to said plurality of phase shifts, such that first phase shift is determined for microwave radiation of a first frequency $F_1$, and a second phase shift is determined for microwave radiation of a second frequency $F_2$, said first phase shift being corrected to form a first measured phase shift according to the equation:

$$Ph_{F_1} = \frac{\Delta Ph(F_2) - \Delta Ph(F_1)}{F_2 - F_1} F_1$$

wherein $Ph_{F_1}$ is said first measured phase shift for said first frequency $F_1$; and $\Delta Ph(F_1)$ and $\Delta Ph(F_2)$ are said phase shifts for $F_1$ and $F_2$; and wherein a first corrected phase shift is formed according to the following equation:

$$(Ph_{F_1} \mod(360)*360) + \Delta Ph(F_1) = P_{true}$$

such that $P_{true}$ is said first corrected phase shift; and
(f) determining the moisture content according to a ratio of said corrected phase shift and said attenuation.

* * * * *